United States Patent [19]
Staggs

[11] Patent Number: 6,063,381
[45] Date of Patent: May 16, 2000

[54] THERAPEUTIC USES OF PUNGENT BOTANICALS AND THEIR RELATED COMPOUNDS

[76] Inventor: Jeff J. Staggs, 7474 E. Arkansas Ave. #8-10, Denver, Colo. 80231

[21] Appl. No.: 08/338,489

[22] PCT Filed: May 19, 1993

[86] PCT No.: PCT/US93/04763

§ 371 Date: Mar. 18, 1997

§ 102(e) Date: Mar. 18, 1997

[87] PCT Pub. No.: WO93/23061

PCT Pub. Date: Nov. 25, 1993

[51] Int. Cl.$^7$ ............ A61K 35/78; A61K 31/16
[52] U.S. Cl. ............ 424/195.1; 514/627; 514/858
[58] Field of Search ............ 424/195.1; 514/627, 514/858

[56] References Cited

U.S. PATENT DOCUMENTS

| | | | |
|---|---|---|---|
| 4,536,404 | 8/1985 | Bernstein | 514/627 |
| 4,939,149 | 7/1990 | Blumberg | 514/691 |
| 4,997,853 | 3/1991 | Bernstein | 514/626 |
| 5,008,289 | 4/1991 | Berstein | 514/159 |
| 5,021,450 | 6/1991 | Blumberg | 514/453 |
| 5,063,060 | 11/1991 | Berstein | 424/422 |

OTHER PUBLICATIONS

Cavallito, C.J.. Antibiotics From Plants, in *Medicinal Chemistry,* 1951, p. 248.
Chaurasia & Kher. "Activity of Essential Oils of Three Medicinal Plants Against Various Pathogenic and Nonpathogenic Fungi" in *Indian J. of Hosp. Pharm.* (1978), 15(5), pp. 139–141.
Duke, J.A. *Handbook of Medicinal Herbs.* 1986, pp. 98–99, 382–383.
Herbort et al. "Role of Peptidergic Neurons in Ocular Herpes Simplex Infection in Mice" in *The FASEB Journal.* Nov. 1969, pp. 2537–2541.
Hoffman, D. *The Herbal Handbook.* 1967, p. 59.
Hoffman, P. et al. "Separation and Quantitation of Red Pepper Major Heat Principlas by Reverse–Phase High–Pressure Liquid Chromatography" i *J. Agric. Food Chem.* 1983, 31, pp. 1326–1330.
Jain and Jain. "Authorized Studies on Some Indigenous Volatile Oils and Their Combinations" in *Planta Med.* 1972, 22(2), pp. 136–139.
Kloss, Jethro. *Back to Eden.* 1988, pp. 122–133, 284, 484–488.
Levy, Juliette de Bairacli. *The Illustrated Herbal Handbook for Everyone.* 1991, pp. 49–50, 222.
Levy, Juliette de Vairacli. *The Complete Herbal Handbook for Farm and Stable.* 1991, pp. 273–276, 303–304, 331, 355–357, 401–402, 410–411.
Loder, J.W. et al. "Tumor Inhibitory Plants. Amides of *Piper Novae–Hollandiae* (Piperaceae)" in *Aust. J. Chem..* 1969, 22, pp. 1531–1538.
Lust, John. *The Herb Book.* Jun. 1983, p. 167.
*The Merck Index.* 1996, pp. 287–288, 1285–1286.
Quisumbing, Edwardo. *Medicinal Plants of the Phillipines.* 1951, p. 215–217, and 835–838.
Tierra, Michael. *The Way of Herbs.* May 1983, pp. 41–42, 46–47, 133.
*de Bairacli Levy, Juliette. *The Complete Herbal Handbook for Farm and Stable.* 1991 pp. 275, 276, 331, 401, 402.
*de Bairacli Levy, Juliette. *The Illustrated Herbal Handbook for Everyone.* 1991, pp. 49, 222.
* Kloss, Jethro. *Back To Eden.* 1988, pp. 128, 484, 485.
*Cavallito, C.J.. *Antibiotics From Plants, in Medicinal Chemistry.* 1951, p. 248.
*Quisumbing, Eduardo. *Medicinal Plants of the Phillipines.* 1951, pp. 216, 217.
Duke, Purseglove, *Chemical Abstracts* 97(11): 92598e, 103 (25): 210886q, 112(19): 175337y, and 116(3): 18385c of record IDS, or OA in prior case #07/886,640 filed May 21, 1992. of record in IDS of prior case #08/376,045 filed Jan. 20, 1995.
Tierra, Michael. *The Way of Herbs.* May 1983, p. 133.
Lust, John. *The Herb Book.* Jun. 1983, p. 167.
Chaurasia et al., "Activity of essential oils of three medicinial plants against various pathogenic fungi", (1978) Indian J. Hosp. Pharm. 15(5) pp. 139–141.
Jain et al. "Antifungal studies on some indigenous volatile oil and their combinations", Planta. Med. (1972) 22(2), pp. 136–139.

*Primary Examiner*—Kevin E. Weddington

[57] ABSTRACT

A new class of general antiinfective agents extracted from pepper, ginger, and other plant species containing vanillyl and piperidine ring structures typical of the pungent principal found in pepper and ginger. The role of these structures, their attached hydrocarbons groups, and other agents found with the plant extract is demonstrated in the topical treatment of dermatophyte infections, tissue injuries, and abnormal proliferations of keratin.

19 Claims, 7 Drawing Sheets

PHENOL C$_6$H$_5$OH

ORTHO-METHOXYPHENOL CH$_3$OC$_6$H$_4$OH

VANILLYL (CH$_3$O)(OH)C$_6$H$_3$-CH$_2$

3-METHOXY-4-HYDROXYBENZYLAMINE $(CH_3O)(OH)C_6H_3-CH_2-NH_2$ where R is an organic hydrocarbon group

VANILLYLAMIDE $(CH_3O)(OH)C_6H_3-CH_2-NH-R$

| STRUCTURAL FORMULA | CAPSAICINOID |
|---|---|
| $R'-CO-(CH_2)_4-CH=CH-CH-(CH_3)_2$ | CAPSAICIN |
| $R'-CO-(CH_2)_6-CH-(CH_3)_2$ | DIHYDROCAPSAICIN |
| $R'-CO-(CH_2)_5-CH-(CH_3)_2$ | NORDIHYDROCAPSAICIN |
| $R'-CO-(CH_2)_9-CH-(CH_3)_2$ | HOMODIHYDROCAPSAICIN |
| $R'-CO-(CH_2)_5-CH=CH-CH-(CH_3)_2$ | HOMOCAPSAICIN |
| $R'-CO-(CH_2)_7-CH_3$ | NONANOIC ACID VANILLYLAMIDE |
| $R'-CO-(CH_2)_8CH_3$ | DECANOIC ACID VANILLYLAMIDE |

CAPSAICINOIDS

PIPERIDINE $(CH_2)_5NH$

PIPERINE

PIPERYLINE

PIPERETTINE

PIPEROLEIN A

PIPEROLEIN B

PIPERANINE where R" =

PUNGENT ALKALOID PRINCIPALS OF PEPPER

EUGENOL $C_{10}H_{12}O_2$

CURCUMIN $C_{21}H_{20}O_6$

Gingerol  Shogaol $C_{17}H_{24}O_3$ (where n = 4, 6, or 8)

Paradol  Zingerone $C_{11}H_{14}O_3$

GINGEROLS

RESINIFERATOXIN

TINYATOXIN

THERAPEUTIC USES OF PUNGENT BOTANICALS AND THEIR RELATED COMPOUNDS

This application is a 371 of PCT/US93/4763 filed May 19, 1993.

TECHNICAL FIELD

The invention relates to a new class of general antiinfective compounds obtainable from plant species of the pepper, and ginger families, and chemically related species that are also useful in the treatment of tissue injury, and skin disorders.

BACKGROUND ART

There is a wide array of microorganisms that are pathogenic to man, and other organisms. Pathogenic bacteria, viruses, rickettsia, and fungi may cause disease in their host organism whether plant, animal, or man.

Fungal diseases of man and animals, often referred to as mycoses, may be classified into two broad categories. Deep tissue, or systemic mycoses involves the wide dissemination of pathogenic fungi growing in internal organs, and tissue, and superficial mycoses, which generally represent different types of pathogenic fungi than those that infect the skin, hair, nails and mucosa.

Deep tissue mycoses including aspergillosis, actinomycosis, blastomycosis, coccidioidomycosis, cryptococcosis, histoplasmosis, nocardiosis, paracoccidioidomycosis, entomophthoromycosis and occasionally candida, may infect the lungs, brain, bones, spinal fluid, liver, heart, kidneys, and other internal organs, as well as the skin. Depending on severity, deep tissue mycoses may cause illness that ranges from asymptomatic to life threatening.

Superficial mycoses, also called dermatophytosis, describe disorders such as ringworm, athlete's foot, favus and candida, which infect the skin, hair, nails and mucosal linings. There are perhaps three dozen or so known species of pathogenic fungi, and yeasts responsible for causing these diseases.

The National Health Survey of 1971–1974 projected from its sampling that about one out of every twelve people in the United States had some form of dermatophytosis, with men being four times more likely than women to contract infections.

Surveys of other nations reveal a much higher incidence of superficial mycotic diseases, among the poor, and underdeveloped countries of Africa, Asia, South America, and those areas of the world having tropical climates.

Tinea is another term used to describe ringworm. It is usually followed by another term which describes the particular location of the infection. Hence, athletes foot is often referred to as "tinea pedis". Scalp ringworm is also known as "tinea capitis"; body ringworm as "tinea corporis", jock itch as "tinea cruris" etc. Though not considered to be life threatening, as some deep tissues mycoses can be, superficial mycoses assuredly take a fair toll of man and animals in misery, inconvenience, and expense.

Though not classified as a serious illness by the medical profession, this does not necessarily reflect the view point of those sufferers of superficial fungal infections. On a personal level, an athlete whose performance on the playing field is diminished because of painful cuts on the feet due to an athlete's foot infection, may consider it to be a serious illness.

A young woman who develops bald patches on her scalp due to ringworm may feel that she has a serious illness. It is also likely that she may feel the same about a ringworm infection of the fingernails, where the nails assume a horrible, unsightly appearance as a result of thickening, brittleness and discoloration typical of the disease. Add to this a year and a half of systemic treatment to see results, and she may feel that she indeed has a very serious illness.

Do people who are unemployed, low income, or without medical coverage consider an illness, that in addition to causing discomfort, can cost them several hundred dollars a year in treatments, and still not be cured? Do ranchers think of ringworm as a serious disease, when the feed lots, who are paying high prices for livestock, refuse their herd because of ringworm? I think the answer is a resounding "yes!."

Antibiotic drugs such as penicillin, tetracycline, and sulfa ect., though often effective in the treatment of bacterial infections, are useless against infections caused by viruses, rickettsia, and fungi. Fungal disorders, for example require treatment with a separate group of antimicrobial drugs, known as antifungals, or antimycotics.

Antimycotic drugs (FIGS. 14–16) were first introduced in the 1950's with nystatin (1954), amphotericin B (1958), and griseofulyin (1959). These drugs were originally administered systemically. Tolnaftate (FIG. 17) was introduced in 1965 as the first effective topical antifungal treatment. Since the 1970's, a number of "azole" derivative antifungals such as clotimazole (FIG. 20), miconazole (FIG. 21), econazole (FIG. 22), ketoconazole, and others have made their appearance as antimycotics for both systemic, and topical administration. The more current trend has been toward the developement of a "triazole" (FIG. 23) class of antifungals, including such derivatives as fluconazole (FIG. 24), terconazole (FIG. 25), and itraconazole ect.

Prior art treatments for superficial mycoses, in addition to being expensive, require repeated application before improvement can be seen in the patient. Currently available over the counter treatments, containing clotrimazole, miconazole, tolnaftate, or undecylenic acid, recommend up to sixty applications of the product in order to provide full benefit. More treatments are often required.

Regardless of economic impact, even wealthy individuals, with the best health care available suffer with all the others when it comes to the discomfort, and bother of repeated application of medication that is slow acting, and often ineffective at producing cure or relief of symptoms.

Even prescription topical antifungals, administered by a dermatologist, may require as many as two hundred applications over a period of three months to cure some cases of athlete's foot alone. Nail infections may require eighteen months of multiple, daily treatment to provide cure. In addition to being very expensive and time consuming, applying the medicine repeatedly each day is bothersome. Coupled with the discomfort of the fungal disorder, the expense, and inconvenience associated with the treatment adds further to the misery of the condition.

The current cost of treating ringworm and other superficial mycoses excludes the economically disadvantaged, who suffer most from the condition, from receiving treatment. Poor sanitation, a lower standard of general health, along with the fact that it is rarely treated, adds to the greater prevalence of ringworm, and other superficial mycoses among lower income individuals. To a low income family in the United States, an extra five dollars a week expense to buy the cheaper topical over the counter fungal treatments can cause real hardship on the household budget. For the disadvantaged of many developing countries, five dollars a week looks more like a good wage for a healthy working man supporting a family, than what one can afford to pay to treat a skin condition that takes weeks to cure, if it can be cured at all. For these reasons, superficial mycoses among the poor usually go untreated, being prohibitive because of the cost of treatment.

In this respect, the current array of prior art antifungal treatments have failed to significantly heal superficial mycoses throughout the world, being inaccessible to most of the world because of cost. In addition to the misfortune of not having viable treatment for tens of millions of sufferers of fungal infection, no markets are created, and no products sold, to the advantage of no one. Prior art antifungal treatments keep the price of treatment high, the market volume small, and undiverse, and only bring marginal relief to a relative few of the many suffers.

The bad economics of currently available topical antifungals prohibits their use in the livestock industry, as well. The cost of the medicine, coupled with the labor required for repeated application to livestock, forbids the creation of a significant market for these medicines within the industry. As stated earlier, livestock infected with ringworm are refused by feed lots. The rancher holding them back, in turn, raises his prices to cover this liability; effecting all processors and consumers of meat products.

Ringworm, being highly contagious, can spread through a herd within a few short weeks, not allowing enough time for treatment and recovery in the weeks prior to going to market, even if they are treated. With the current way of topical antifungals, treating food animals for ringworm is an absurd notion. The cost involved in applying a medicine, perhaps fifty times, to a single head of livestock could never be justified. For this reason, treatment is withheld, to the disadvantage of both the rancher and the animal, which in addition to suffering discomfort, spreads the disease to other animals, perpetuating the cycle further. In addition to money lost, no viable solution is offered by pharmaceutical manufacturers which would otherwise enjoy a new, very large potential market.

Whether or not one feels the economic impact of superficial mycoses, all suffers experience the inconvenience of having to make repeated application of currently available prior art topicals. The necessity of making repeated applications is an indication of weak drug action, and that is another great flaw of prior art antifungal treatments.

Systemic antifungal drugs are also used to treat superficial mycoses, in addition to the deep tissue diseases. Drugs like amphotericin B, clotrimazole, enconazole, griseofluvin, ketoconazole, miconazole, and nystatin, are administered internally, usually orally, or by injection. Like the topical antifungals described earlier, most of the systemics treatments require multiple doses in order to be effective. Systemic treatments are the most costly of all, requiring the supervision of a physician. They are most dangerous to the patient, with undesirable side effects that can further endanger the health of the patient. The risk of damage to internal organs, and adverse reactions to other medications, are factors that must be carefully weighed by physicians administering systemic antifungals. With this, other less severe, yet unpleasant side effects, include nausea, vomiting, headache, dizziness, fever, diarrhea, and many other adverse effects that contribute to the misery and ill health of the patient.

Amphotericin B (FIG. 14), given by injection in the treatment of systemic fungal infection, carries with it the risk of liver and kidney damage, and can also result in blood disorders. It interacts negatively with many cardiac medications, and diuretics, as well as other antibiotics.

Griseofulyin (FIG. 16), usually taken orally, for fungal infections of the skin, hair, and nails, has a risk of liver damage. Reduced bone marrow function, with lowered white cell levels is another possible adverse effect of treatment. Drug interactions with anticoagulants, and barbiturates reduce effectiveness, and the risk to pregnancy often forbids treatment.

Ketoconazole, taken orally for systemic fungal infections, also carries the risk of liver damage as a result of treatment. The effectiveness of ketoconazole is diminished by interaction with various antacids, and other gastric medications. Ketoconazole increases the potency of other drugs, and is reduced in potency by some antibiotics.

Miconazole (FIG. 21), taken by injection for fungal infection of the lungs, brain, kidney, and lymph nodes, can alter blood chemistry resulting in anemia. Miconazole also interacts negatively with medications for diabetes, epilepsy and anticoagulants. The effectiveness of amphotericin B is reduced by miconazole.

Nystatin (FIG. 15), taken orally for candida disorders, is of little use in the treatment of systemic fungal infections. Though having far fewer adverse side effects than the other antifungal drugs, it is ineffective against most fungal infections except candida, and aspergillus, making it of limited usage.

Treatment with these systemic antifungals often produces many other very unpleasant side effects, in addition to the adverse effects upon blood composition, internal organs and other medications being taken by the patient. Taken internally, amphotericin B, griseofulyin, ketoconazole, miconazole and nystatin, may cause nausea, vomiting, diarrhea, dizziness, headache, fever and other disorders during the coarse of treatment. These symptoms, though unpleasant enough for the patient, can also lead to more serious complications, further advancing the ill health of the patient. Beside these known adverse effects, others yet unknown, will be discovered with further research. The full effect of internal treatment with antibiotics on the body is a very complex matter, and warranting much caution.

Topical treatment of superficial mycoses is much safer than internal treatments. The prior art, however, has failed to produce topical antifungal medications effective enough to deal with more serious infections. This necessitates the use of systemic treatments, which are more dangerous, costly, time consuming, and associated with many other unpleasant illnesses to treat even superficial mycoses.

The adverse effects of prior art systemic antifungal treatments is a more serious complication of treatment for deep tissue mycoses than superficial mycoses. Patients suffering from deep tissue disorders, such as cryptococcosis, histoplasmosis, blastomycosis, coccidioidomycosis, paracoccidioidomycoses, and others, are generally in a much poorer state of health than patients being treated for dermatophytosis. For this reason, the adverse effects of systemic treatment have greater impact on the overall health of patients being treated for deep tissue mycoses. This is of particular significance in the treatment of immunocomprimised patients.

Deep tissue mycoses find their greatest opportunity in immunocomprimised patients. These include cancer, organ transplant patients, and others on immunosuppressant medication, and particularly with patients suffering from immune disorders such as acquired immune deficiency syndrome, otherwise known as AIDS. These patients, who are very ill indeed, are highly susceptible to infection from these diseases, as their natural defenses against the pathogenic microbes is greatly reduced.

The adverse effects of treatment with currently available prior art systemic antifungals, are devastating to immunocomprimised patients, to the point of being themselves life threatening to the patient- To those patients in greatest need of treatment for deep tissue mycoses, the medication is most dangerous to administer.

With the steady rise in treatment with immunosuppressant drugs, and the much more dramatic rise in the number of cancer, and AIDS cases reported, and anticipated for the future, the demand for safe, effective, and low cost treatments for both deep tissue, and superficial mycoses, is more urgent than ever. The prior art has largely failed to meet this criteria as a result of high cost, low ineffectiveness, and the high toxicity of their antifungal medications.

The focus of the prior art upon the development of azole derivatives, is perhaps largely responsible for keeping the cost high, and the effectiveness of antifungal treatments so low. The newer generation triazole (FIG. 23) derivatives, including fluconazole (FIG. 24), terconazole (FIG. 25), itraconazole, and others, cost many millions of dollars to develop, and apparently are not that much more effective than the prior generation imidiazole (FIG. 19) derivatives, and certainly are doing nothing to make treatment more affordable, or convenient. Beside this, they have much narrower application than the imidiazoles, and are considered auxiliary, and not mainline treatments.

It seems doubtful at this point, that either of the azole groups will produce derivatives of significantly greater effectiveness in the treatment of fungal disorders, than what is currently available with prior art treatments.

DISCLOSURE OF INVENTION

Accordingly, several objects and advantages of my invention include a method for treating fungal infections, otherwise known as mycoses, in which cure is complete with as few as one single application of my medication. Rather than making scores of applications, usually required by prior art antifungal medications, my medication usually requires just one treatment to affect full cure. The effectiveness of my medication is nothing short of astounding, and is truly generations ahead of currently available antifungals.

I have discovered that plants of the pepper family, and plant species with similar chemistry contain active agents that provide complete cure when applied to areas infected with mycotic diseases. These agents may be administered in the wide range of commonly used drug vehicles and carriers, with results that are absolutely unprecedented when compared to prior art treatments.

Tinea, in its various forms, otherwise known as athlete's foot, jock itch, favus, and ringworm, along with other types of dermatomycoses such as candida, may be completely healed after a single treatment with my medication. Topical treatment of these diseases, in the form of an infusion, bath, douche, shampoo, lotion, drops, tincture, plaster, powder, aerosol, or other carriers, all provide outstanding results.

Currently available prior art over the counter topical treatments for ringworm containing clotrimazole, miconazole, tolnaftate, or undecylenic acid, usually require several weeks of daily multiple treatments before improvement can be observed in the condition. In addition to the considerable expense of having to buy several containers of the medication, the time, and inconvenience involved in making repeated applications with meager results adds further to the misery and discomfort of the disease. Even mild to moderate cases of tinea can easily require more than sixty applications of these products before the condition improves. The weak therapeutic action of these prior art, over the counter treatments is often insufficient to produce adequate results, and must be treated by a physician, using prescription topical, and systemic antifungals taken internally.

Prescription treatment with antifungal medications is the most expensive of all treatments. Beside the cost of having an attending dermatologist, the medications themselves are more expensive than the over the counter varieties. This type of treatment, being the best the prior art has to offer, still may require several months of multiple daily doses of the antifungal medication to cure some kinds of ringworm. Treatment for athlete's foot may require up to three months of multiple daily doses of the medicine before the condition can be cured. Ringworm infections of the toe nails can take up to eighteen months to heal! So adding the expense of visits to a dermatologist, time lost from work or leisure, the time and inconvenience of applying the medicine, the cost of the medicine, and the ongoing discomfort of the disorder, all have an economic impact that is quite considerable, in addition to the discomfort of both the disease and the side effects of treatment.

Systemic treatment with antifungal drugs, such as amphotericin B, clotrimazole, griseofulyin, ketoconazole, miconazole, nystatin and others, in addition to being expensive and time consuming, have many bad side effects that can further endanger the health of the patient. These drugs, taken internally, carry the risk of damage to liver and other internal organs, and adverse effects upon blood chemistry. Patients receiving such treatments must be monitored for changes in blood and organ function, as a safeguard against serious damage that can result from treatment. Prior art systemic antifungals also interact adversely with a large number of other medications, another area that requires close attention by the attending physician. Beside this, other adverse effects include nausea, vomiting, diarrhea, fever, headache, and other unpleasant symptoms that accompany the discomfort of the disease.

With my medication, a single topical application is all that is usually required to completely cure most types of dermatophytosis. Even recalcitrant cases of athlete's foot are healed in as few as half a dozen doses of my medicine. Body and scalp ringworm lesions disappear, usually within the first day after treatment, and require no follow up dosages. With my treatment, systemic treatment of superficial mycoses is a thing of the past. Instead of making several visits to a dermatologist, and taking repeated doses of drugs that are expensive, dangerous, slow acting, and create other illnesses as a side effect, one need only make a single, or few topical applications of my treatment for complete cure. In addition to effectiveness that is truly astounding, these pepper compounds are completely safe, being derived from commonly consumed food. Topical applications of my treatment generally require less active agents, than what might be commonly consumed in a meal that includes any of the pepper species. In addition to that, there is no long term, chronic exposure to the medicine, as is required with prior art topical antifungals, that have only a long term therapeutic effect, if any at all!

The prophylactic action of pepper constituents continues to protect damaged tissue from reinfection, by maintaining its antifungal action for days after treatment, in addition to it's direct, and immediate fungicidal action. This further aids rapid healing, by allowing diseased tissue to regenerate, rather than concentrate energy on combating disease Pepper also appears to act as an immunostimulant, by precipitating leukocytes, and other mononuclear cells, along with a variety of antifungal compounds from the blood, and surrounding tissue, to the area of infection. Though done primarily through inducing inflamation, pain and discomfort are not required in order to receive the full therapeutic benefit. Pepper compounds are also believed to aid in the delivery of these antifungal immune resposes of the body, and increase their potency in addition to its own antifungal actions.

Healing, and excellerated regeneration of diseased tissue is another important therapeutic action opepper compounds. While whole, healthy skin is the best protection against infection from dermatophytes, pepper's ability to regenerate diseased skin is equally astounding to it's antifungal action.

The healing, and tissue regeneration actions are further demonstrated in the treatment of other forms of dermatitis such as dandruff, seborrhea, eczema, warts, corns ect. These chronic skin disorders, which are not currently recognized as being of microbial origin, also respond with complete cure when treated with pepper compounds, often in the same way as superficial mycoses. These diseases, for which the prior art believes incurable, may also be completely cured with my invention, often as easily as superficial mycoses such as ringworm are cured.

In a study of eight patients, all infected with various forms of dermatophytosis, complete cure is obtained after one topical application of the medication of the current invention in five of the eight cases studied. The other three cases studied are cured within half a dozen treatments or less. None of the patients are taking any kind of medication for ringworm, or for any other disorder, and no special sterilization measures of clothing, furniture or bedding are taken, beyond otherwise good personal hygiene.

In the first portion of the study, a family of three, all afflicted with ringworm, are completely healed after a single topical treatment with a pepper compound.

The infant has developed approximately six ringworm lesions about the back of the scalp, and back, and right side of the neck. The first few lesions were noticed a month before.

The mother of the infant has about six ringworm lesions on the right arm, most on the outside bicep. The appearance of the lesions was first noticed approximately three months before.

The father of the infant has approximately eight ringworm lesions on the left arm, most on the outside bicep. The right arm has four lesions, also on the outside of the bicep. Four other lesions appear on the shoulders, and lower back. The man first noticed lesions of this type approximately eight years earlier.

On all three subjects, the ringworm lesions have the same general appearance. The lesions are ring shaped, with slightly raised outer borders that are sometimes crusty. The lesions are red, with a smooth, and sometimes scaly interior. A clear, sticky fluid sometimes covers the lesion. The average diameter of the ring is about 15 mm (0.6"), with some as large as 20 mm (0.8"). The lesions appear, and remain for several weeks, sometimes disappearing, leaving lighter colored skin at the site of the prior lesion.

The man is first to be treated with a preparation of capsicum, wherein a plaster is applied to three lesions on the left bicep. A very slight, momentary tingling sensation is reported. The sensation lasts for about the first five minutes after application, and is not uncomfortable. The plaster is left on the skin for about one hour, then rinsed off with water. Afterward, the lesions appear redder than they did prior to application of plaster. After six hours, the lesions appear to be whiter, with the coloration being more similar to the skin tone of the healthy skin, than prior to treatment. At twenty hours, all three lesions appear healed, as it requires very close examination to reveal the site of the prior lesion. The characteristic patch of lighter colored skin that normally accompany lesions that have healed by themselves is not present.

The other dozen or so lesions found on the man are examined, and found to be substantially unchanged from their last examination the day before. Another examination on the third day yields the same results, with no sign of the three lesions that were treated and healed, and little change in the untreated lesions.

Also, on the third day after initial treatment, the other dozen ringworm lesions on the arms and trunk of the man, are treated with the same capsicum plaster, with identical results. All twelve lesions, regardless of location, are healed with the exact location of the prior lesion being difficult to determine because of the advanced degree of healing of the skin in that area.

One week later, the woman is treated with the same capsicum plaster as the man, with similar results. At three days after treatment, all six lesions are completely healed in similar fashion to those on the man.

One week after the woman is treated, the infant girl is also treated with the capsicum plaster in the same manner as both her parents, and is healed in the same way, with the disappearance of all lesions within about one day. It is also interesting to note that the infant girl displays no sign of discomfort when the medication is applied, and does not cry, or even appear to take notice of the treatment.

Regular examinations of these three patients, over a period of several months, fails to identify the reappearance of one single ringworm lesion in any one of them. Each lesion of the patient is completely healed of ringworm, after just one single topical treatment with my medicine. 100% cure of twenty-eight lesions on three subjects is accomplished after a single dose of my medication, without reappearance of a single lesion. This is done without sterilization measures, and aside from any other medication whatever.

In another portion of the study, a woman in her middle thirties is healed of athlete's foot within hours of a single treatment of my medication. The woman works a full time job, in which she is required to be on her feet most of the time. Approximately one week after having purchased a more comfortable pair of shoes for work, the woman develops an inflammatory variety of athlete's foot. The primary symptoms are intense itching on top of the toes and foot, felt mostly in bed at night, along with a bad, musty foot odor. The itching is now interfering with sleep each night.

The woman soaks her feet in a bath, prepared from infusion of capsicum, for fifteen minutes. The woman reports a warm, tingling sensation that lasts about ten minutes. This treatment is administered at 8:00 p.m. The woman retires for the evening at 10:00, and does not experience any of the itching characteristics of the previous evenings. For three weeks the woman reports not a single recurrence of the itching on the feet. She continues to wear the same footwear as before, and does not take any kind of sanitary, or other precautions to avoid reinfection.

After about three weeks, the woman begins to notice a gradual return of the itching on top of the feet that she had experienced before. Within another week or two, the itching is as intense as ever, and is again interfering with sleep.

The woman's feet are treated with a lotion of capsicum, using raw aloe vera gel as the lotion carrier. Lotion is applied to the feet, and rinsed off with water at the end of half an hour. The treatment is administered at 8:00 in the evening, before the woman retires for the evening at 10:00. The woman reports no itching that evening, nor afterwards, for many months. She disposes of the comfortable shoes, she had bought for work, and has no further recurrence of athlete's foot symptoms. The woman is completely healed of athlete's foot after just one single treatment with my medication!

The sixth case involves a five year old girl, who is completely healed of a recalcitrant case of dry athlete's foot. Prior to treatment, the child's feet are peeling severely in the areas between the toes, and on the entire sole of the foot. Loose skin, in pieces as large as about 4 mm (1/8") square are hanging around the lower edge of the ball of the foot. The entire sole of the foot is calloused, and has a wrinkled appearance. Deep cuts occur periodically on the ball of the foot and around the base of the toes, particularly the great and small toes. The child often complains that her feet hurt from the cuts, but otherwise describes no other discomfort or symptoms. The girl has had these symptoms for about three years, since age two years.

At age two years, the girl develops a particular affection for a certain pair of shoes, and wears them constantly, refusing to wear other shoes. Weeks later, the girl develops a very offensive foot odor. Afterward, her feet gradually develop the symptoms described above, becoming chronic over the next three years.

An ethanol tincture of capsicum is applied to the girl's feet. The girl complains about a stinging sensation in the cuts around her great and small toes. The girl cries for about five or ten minutes, then reports that the sting is gone. The girl is also treated with the same capsicum tincture on days three and five, after the initial treatment. The investigator performs these second and third treatments because he is not sure if the first treatment is sufficient to penetrate such thick callouses on the soles of the feet, having never treated such badly damaged skin with this particular treatment. On day three, just prior to the second treatment, the feet are examined and appear slightly improved. The cuts around the toes have formed scabs, and no discomfort is reported by the girl after application of the tincture.

On day five, the feet are again examined before receiving the third treatment, and again appear to be further improved. The cuts are continuing to scab over and heal, and the girl reports no discomfort from the medicine. This general trend continues for the next several days, yet treatment is not again administered.

By the fourteenth day, the feet are nearly, completely healed. There are no cuts or scabbed cuts, and no peeling or loose skin. The callouses are nearly, completely reduced, and the skin has a healthy color and texture, and no longer has a wrinkled, ragged appearance. It is not possible to determine that the girl has ever had athlete's foot, as her feet are healthy and normal. The child is excited that her feet are "like new again".

On day twenty one, the girl's feet are again examined. The skin around the bottom and sides of the toes has succumbed to reinfection, as the skin is again peeling, though not as severely as before the first treatment.

At six weeks, the girl's feet have returned to the pretreatment condition. The skin on the sole of the feet is thickened and calloused. The skin on the soles and between the toes is peeling and has a ragged appearance. Cuts appear periodically at the base of the toes, on the heel and at the ball of the foot. The dry athlete's foot is back in full force.

The reinfection of the girl's feet is not presumed to be the result of recontamination, as no sanitary measures have been taken to prevent reinfection, and the girl continues to wear the same footwear as before the treatment. As these pathogenic fungi find opportunity in damaged skin tissue such as that described, the skin must be healed to prevent reinfection. The best protection from reinfection being healthy, undamaged skin.

This is one reason why the prior art has such difficulty curing this type of ringworm. The therapeutic action of prior art antifungals is so weak and slow acting, it arrests the resident fungi only enough to allow the healing process of the skin a slight advantage.

This is why a case of dry athlete's foot can easily require twelve weeks of daily, multiple treatments with prior art medications to provide cure, which is usually only temporary.

The dramatic improvement of the girl's feet between the last treatment on day five, and the examination on day fourteen, suggests accelerated healing over any activity of fungi during this interval. It also suggests a prophylactic action by my medicine that may provide protection for perhaps seven days or more.

Recalling complete cure after a single dose of my medicine in the first five cases leads to the conclusion that the fungi are eradicated on initial contact with my medication. What distinguishes them from this sixth case is the relatively minor degree of skin damage they suffered, in relation to the present case. This further supports the notion of the prophylactic action of my medicine, as seven days or less is ample time to heal the minor skin damage caused by the body ringworm lesions.

In an attempt to determine the maximum duration of capsicum's prophylactic effect, and to compare it's performance with that of synthetic capsaicin, the synthetic version of the primary irritant found within natural capsicum, the girl's feet are again treated.

Prior to treatment, the girl's feet have again returned to their original, recalcitrant condition that was noted prior to the first treatment. The girl's feet are peeling severely on the bottom and sides of the toes, and on the ball of the foot. The skin in this area is thickened, and calloused, with deep cracks sometimes resulting in painful cuts. The skin has a wrinkled, dry, and ragged appearance, with intermittent red blotches, occupying about half the total surface area. Small cuts appear periodically around the base of the great and small toes, which often cause pain, especially when walking.

A lotion of capsicum, consisting of 4 cm$^3$ (1/4 teaspoon) of ground red pepper mixed with 48 cm$^3$ (12 teaspoons) of raw, aloe vera gel, is applied to the child's left foot. The girl describes a tickling sensation as lotion is being applied, and is laughing. About three minutes afterward, the girl begins crying, saying that the cuts on her toes are burning. She continues to cry for about ten more minutes, and afterward indicates that the burning has gone.

At the same time, an ointment of capsaicin, consisting of about 0.03 percent capsaicin (from oleoresin) in turpentine oil is applied to the right foot. There are no cuts on the right foot at this time, and the girl reports no discomfort from the medication.

The medications described above are applied once each week for the next two weeks, and observed regularly over the next three weeks, with little notable change the first few days.

On day three, the feet are examined, and appear to be showing signs of improvement. The peeling does not seem as severe, and the red blotches look as if they are fading. The cuts on the left foot are healing, and show no sensitivity when firmly squeezed with the fingers.

On day four, the feet are again examined, and look much better than the previous day. The peeling is again reduced, and the red blotches have completely disappeared. The right foot looks slightly better than the left, suggesting the therapeutic effectiveness of the capsaicin ointment. The cuts on the left foot show further progress in healing.

Upon examination on the sixth day after treatment, the child's feet look very much improved. The loose skin has for the most part worn away, being replaced by healthy skin that shows no scaling, or discolor. The cuts on the left foot have disappeared, and both feet show reduced skin thickness, and only faint reminder of cracks that are mostly healed. Both feet look about the same, suggesting equivalent therapeutic performance between capsicum and capsaicin preparation.

The examination of day seven reveals little change in the condition of the feet from day six except that they appeared slightly better on day six. Small cuts along the base of the small toe on the right foot are not causing discomfort, as the medicine is applied for the second time.

Subsequent examinations of the next seven days reveal a similar pattern to that of the prior week. Little change is observed the first few days after treatment, with very noticeable improvement being observed between the fourth and sixth day after treatment. This pattern is also established on days eleven through thirteen, yet without substantial advance in the stage of healing beyond that observed on the sixth day.

It is evident that a single weekly application of my medicine produces substantial improvement in recalcitrant cases of athlete's foot. Though this improvement is sustained, it is not usually sufficient to induce full cure, at least within a three week span. Nor does the degree of improvement compare to the results of the prior study, in which the medication was applied three times within the first week. Depending upon the case, two to four applications per week should be sufficient to provide complete, and sustained cure for recalcitrant cases of athlete's foot.

To demonstrate a complete cure for recalcitrant athlete's foot, and to compare the performance of a red pepper (capsicum frutescens) extract with that of one made from black pepper (piper nigrum), the girl's feet are again treated. The girl's right foot is treated with an ethanol tincture of capsicum made from ground red pepper, while the left foot is at the same time treated with a similar tincture prepared instead with an equal amount of black pepper. The girl's feet are treated eleven times, once every other day, over a period of three weeks. The pattern of previous tests is also observed in this trial, with both the red, and black pepper tinctures performing with equal effectiveness. As in the other tests with the girl, significant improvement is observed between the fourth, and sixth day after treatment, with dramatic improvement being noted at two weeks. At three weeks, very little sign of the prior disorder remains, and the condition does not return after weeks of observation. The girl is healed of recalcitrant athlete's foot, with just eleven topical treatments over a period of less than three weeks.

In the seventh case study, a woman of sixty is cured of a dry variety of athlete's foot. Prior to treatment, the woman's feet have peeling skin between the toes, and thickened soles with cuts on the underside of the heal.

The woman's feet are soaked in a capsicum tea for fifteen minutes at a time, once a day, for five days. On the second day, the woman complains that her feet are very dry, and that one of the cuts on her heel is making walking difficult because of the pain. By the fourth day, she indicates the cessation of those symptoms. After eight weeks, the feet are examined and the skin appears healthy, with no sign of peeling or thickening of the skin. The woman indicates that after the fourth day of treatment, she did notice the reimmergence of symptoms at the time of the eight week examination, and felt cured since.

In the eighth case study, a boy of thirteen is completely healed of a severe fungal infection of the face, and neck after just two weeks of treatment with my medication.

Over a period of nearly five months, the boy has been suffering from what is described as an angry, bright red rash about the face, from beneath the eyes, down to the bottom, and sides of the neck. The boy's father describes the disorder as "literally eating his son's face away." The boy, and his family are for some time quite distressed, as treatment administered by a general practitioner, and two dermatologists over more than four months, fails to heal the condition. The expense of treatment is nearing $1,000 out of pocket. The visits to the physician, have cost the parents more than twenty hours away from work, and the boy must be excused from school the same amount of time. The boy is of coarse doubly distressed, as in addition to the discomfort of the disease, he must bear the humiliation of wearing this rash on his face that is more horrible in appearance than a severe case of acne!

A skin scraping sent to a laboratory reveals the presents of fungal hyphae, not of the ringworm variety.

The boy is given griseofulyin orally, but must discontinue treatment after one week as a result of severe nausea. The boy is then given tolnaftate topically, and has shown no significant improvement in the condition over a period of several weeks.

The boy is then given lotion prepared with capsicum, and instructed to apply the medication once every other day after bathing until symptoms disappear. All other treatments are also discontinued.

The boy's father administers the treatment as prescribed, and is seeing noticeable improvement by the third day. The condition continues to improve over this period, and by the tenth day the skin is almost completely healed, with barely a remanent of the prior disease remaining. To say the least, the boy's family and friends are amazed, and astounded at the rapidity of cure of this horribly unsightly condition, that had persisted for so many months before without improvement, often referring to the medicine as "a literal Godsend!"

The treatment is discontinued after only two weeks, and the boy is healed without relapse after many weeks of observation even until the time of this writing.

As can be seen from these several examples, the effectiveness of my topical antifungal medication is truly astounding. Single application cure of dermatophytosis, being unheard of among prior art treatments, is the usual result with the medication of my invention. No longer is it necessary for suffers to endure prescription therapies, which are slow acting, time consuming, expensive and potentially dangerous with many other unpleasant adverse effects. With my medication, embodied in the form of a topical, over the counter treatment, even recalcitrant cases of athlete's foot can be cured with a few periodic applications of my medicine. Instead of months of antibiotic therapy, administered by a dermatologist, the sufferer can cure the condition themselves, with a safe, inexpensive and astonishingly power medicine, such as mine.

The savings in health care cost that my invention provides for the treatment of dermatophytosis alone is astronomical. Prior art treatments, that cost many hundreds of dollars and represent considerable loss of time from work and leisure, are no longer required. With my medication, these same disorders can be cured for pennies, with only minutes of time required by the sufferer, and without the attention of a physician.

With the very considerable cost savings my medicine provides, the sufferer also gets prompt relief from the symptoms of dermatophytosis. Instead of waiting days, or weeks to gain relief from ringworm itch, as is the requirement of prior art topicals, my treatment provides relief in just minutes! Instead of enduring weeks, or months of systemic antifungal treatment to see improvement in a recalcitrant case of athlete's foot, with my treatment, dramatic improvement is seen within hours, to a few days of the first treatment. The savings here, in terms of human discomfort and inconvenience is incalcuable.

The amazing healing power of my medicine, coupled with tremendous economic advantage it provides, opens the doorway for the creation of many new, and very large markets for topical treatment of superficial mycoses. Rather than exclude the economically disadvantaged from a viable treatment, as prior art antifungals do because of their high cost, and lack of effectiveness, my treatment can be produced and sold at a very low price relative to prior art topicals, and still provide a very large profit margin for marketers. My product will greatly expand the market base for ringworm medicines, by tens of millions of individuals worldwide, and most important, provide effective medical care for those in greatest need of it. Severe cases of ringworm can be completely cured for less than a penny in actual cost of the active agents within my medication. If such a product is sold for a dollar, it would open the market up to many millions of people world wide, and provide a tremendous commercial opportunity for drug manufacturers.

In the United States, a topical ringworm treatment, such as mine, costs less to produce than the current prior art over the counter brands, yet, is scores times more effective. If sold at competitive prices to prior art brands, the superior effectiveness of my medication will radically outsell the competitor brands. The high effectiveness of my treatment will also attract the purchase of low income individuals, who otherwise are not able to afford prior art medications. Because of the need to purchase several containers of prior art over the counter topical treatments to cause even temporary cure, of a single case, low income people do not buy the medication because of the cost, and simply go untreated. In addition to adding more misery to their already unfortunate circumstances, it further contributes to the spread of the disease, thereby perpetuating this undesireable cycle.

Prior art topical treatments for dermatophytosis, such as clotrimazole, miconozale, tolnaftate, and undecylenic acid, are not effective for dealing with the problem. Their weak drug action, coupled with their high prices, preclude their use among the economically disadvantaged and have not been able to establish a market for them.

The expense and weak action of prior art antifungals has also occluded creation of a market for treatment of ringworm, and other superficial mycoses within the livestock industry. The current economics of treating food animals for ringworm, with available prior art treatments, forbids the practice. The economic impact of ringworm within the livestock industry is felt first by the rancher, whose head are refused by the feed lot because of it. Being highly contagious, and finding particular opportunity under certain weather conditions, an outbreak of ringworm can infest a herd within a very short amount of time, and prevent them from market. This economic liability is then added to the cost of the food product, which eventually impacts everyone. Ringworm and other superficial mycoses are just another business liability, for which prior art treatments have failed to remedy, much less establish a market for.

With the treatment of the current invention, the combination of unprecedented effectiveness, and lower cost, make it now economically feasible to establish a product for treatment of ringworm, candida, and other superficial mycoses, within the livestock industry. My medication is especially appropriate for this application, being itself derived from food compounds, generally recognized as safe (GRAS) by the U.S. Food and Drug Administration. With my medicine, an outbreak of ringworm among a herd of livestock within the last week before market, need no longer prevent them from market as before.

The astonishing effectiveness of my medicine, in comparison to prior art topical and systemic antifungals, has crucial bearing in the treatment of deep tissue, as well as, superficial mycoses. The common interchangability of currently prescribed prior art medications between topical and systemic administration, suggests the use of my invention for systemic treatment of deep tissue mycoses as well. As prior art antifungals, such as amphotericin B, econazole, griseofulyin, ketoconazole, miconazole, nystatin, and related drugs are administered as systemics, as well as topicals, my treatment shows excellent promise as a systemic antifungal, as well as a topical.

The active principals found within capsicum, and piper species, and related families provide an important research tool in the systemic treatment of deep tissue mycoses, such as aspergilliosis, actinomycosis, nocardiosis, cryptococcosis, histoplasmosis, blastomycosis, coccidioidomycosis, paracoccidioidomycosis, entomophthoromycosis, candidiasis, and others. Pepper extracts may be given by injection into the blood, spinal fluid, or directly into diseased tissue. Analogs of these active constituents may be developed for oral administration, however, some modification of the molecular structure may be required to prevent decomposition of the active agents that occur as a result of digestive processes.

With the very rapid increase in the incidence of deep tissue fungal disorders, and projections suggesting even greater increases for the future, the need for more powerful, safer treatments is more crucial than ever. Finding opportunity in immunocomprimised patients such as cancer, organ transplant patients, and others on immunosuppressant drugs, and those suffering from AIDS: these diseases are life threatening. Also life threatening to these patients is systemic antifungal treatment with prior art medicines. Their high toxicity, and multiple adverse side effects, often have devastating impact on the health of these patients, who are already very sick. Complications arising from treatment with prior art antifungals can end their life, in addition to adding additional misery to their already tragic circumstances.

Even immunocompetent patients can become very ill as an adverse effect of systemic antifungal treatment. Serious adverse effects include damage to liver, kidneys, and other internal organs. Changes in blood composition often lead to enemia. Less serious adverse effects, yet ones that are capable of causing considerable misery for the patient include nausea, vomiting, diarrhea, dizziness, headache, fever and other disorders. These adverse effects are hard enough to bear for an otherwise healthy patient being treated for athlete's foot, let alone a patient having just undergone an organ transplant, or in the advanced stages of AIDS, or cancer!

Pepper, on the other hand, being itself a food compound consumed by man, is good for the body, not harmful as the prior art antifungals can be. All of mankind, throughout the world has used these plants for food, and from long experience of thousands of years, knows them to be safe and healthful to the body. Pepper compounds, being far less toxic than prior art antifungals, will not induce further illness in the patient, like prior art treatment, as dosages are usually less than the amounts commonly eaten at one time by those who enjoy the fruit, or spice.

Solanacea, piperacea, and related species of plants are widespread throughout the world, and are grown in virtually every country of the world. Their active constituents have all been synthesized, and some can be obtained very cheaply from existing commercial sources. Pepper extracts are versatile, and work very well in all conventional drug vehicles and carriers, allowing for the maximum amount of product embodiments.

Today, more than every before, the importance of having medications that are not only safe, and effective, but cost effective as well, is becoming critical to the preservation of our very way of life. The escalating cost of health care in the United States is causing real hardship on the middle and lower economic classes to the extent that about 1 in 6 americans cannot even afford health care insurance.

Health care costs are consuming a greater share of the middle class budget with each new year. Money that would otherwise be spent on better housing, college educations, early retirement, entertainment, and many consumer goods must instead be spent to cover the cost of health care. In addition to lowering the standard of living for our citizens, it takes much needed capital away from many key industries that provide employment for our citizens and create tax revenues that pay the national debt, and support our government.

Rising health care costs have excluding our lower income citizens from adequate medical care, and are the primary contributor to the national debt. They are moving this country, and others closer, and closer toward economic ruin, while excluding increasingly larger segments of our society from adequate health care. How is a society benefitted by a system that provides adequate health care at the cost of economic ruin? At best, that is merely trading one illness for another, i.e., a physical illness for an economic one.

A medication, such as put forth by the current invention, counters this trend of escalating health care costs being economically, as well as medically therapeutic. It is very safe, and of unprecedented effectiveness. It provides far more complete, and rapid cure of disease than prior art medications, and at a cost of just pennies on the dollar.

The concepts set forth by the invention further serve as a model by which government medicaid, and medicare programs would save hundreds of millions of dollars each year in expenditures. Nationally, the total savings in Gross National Product for the United States could exceed 20 billion dollars annually if the treatment for dermatophyte infections alone were fully implemented.

While providing considerable savings to each nation of the world, my medication will greatly expand the size of the antifungal drug market. The economically disadvantaged throughout the world, who are currently excluded from this market because of high cost, and weak performance of the prior art over the counter topical treatments, will purchase my product because of its dramatic effectiveness. New veterinary uses, not currently existing, will also contribute to a larger consumer market than ever before. Add to this an overseas market, aimed at producing a product for developing countries, and the total consumer base for these products will expand by hundreds of millions of individuals, currently excluded from the market by the high cost, and ineffectiveness of prior art treatments.

Now, and finally, an antifungal treatment exists that can save our nation alone, billions of dollars each year in the treatment of dermatophyte infections alone. A drug that will greatly expand the size of the market for antifungal treatments, bring rapid cure to tens of millions of suffers in our country, and around the world, and provide an important weapon in the war against the more serious infectious diseases that will save lives as well.

BRIEF DESCRIPTION OF THE DRAWINGS

FIG. 2 is a molecular diagram of ortho-methoxyphenol.

FIG. 3 is a molecular diagram of vanillyl.

FIG. 4 is a molecular diagram of 3-methoxy-4-hydroxybenzylamine.

FIG. 5 is a molecular diagram of vanillylamide.

FIG. 6 is a molecular diagram of the capsaicinoids.

FIG. 7 is a molecular diagram of piperidine.

FIG. 8 is a molecular diagram of the pungent alkaloid principals of pepper.

FIG. 9 is a molecular diagram of eugenol

FIG. 10 is a molecular diagram of curcumin.

FIG. 11 is a molecular diagram of gingerol.

FIG. 12 is a molecular diagram of resiniferatoxin.

FIG. 13 is a molecular diagram of tinyatoxin.

FIGS. 14–25 show molecular diagram of common prior art antifungal drugs.

FIG. 14 is a molecular diagram of amphotericin B.

FIG. 15 is a molecular diagram of nystatin.

FIG. 16 is a molecular diagram of griseofulyin.

FIG. 17 is a molecular diagram of tolnaftate.

FIG. 18 is a molecular diagram of ciclopirox.

FIG. 19 is a molecular diagram of imidazole.

FIG. 20 is a molecular diagram of clotrimazole.

FIG. 21 is a molecular diagram of miconazole nitrate.

FIG. 22 is a molecular diagram of econazole nitrate.

FIG. 23 is a molecular diagram of triazole.

FIG. 24 is a molecular diagram of fluconazole.

FIG. 25 is a molecular diagram of terconazole.

BEST MODES FOR CARRYING OUT THE INVENTION

Figure 1:
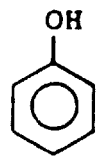
FIG. 1 is a molecular diagram of phenol.

A medicinal preparation of pepper, and its active constituents may be administered in a wide range of conventional drug vehicles and carriers. Capsicum, and black pepper are available commercially as oleoresin, in a wide range of concentrations, and pungencies, and may be used in place of the plant product described below.

The various preparations described below are made from a moderate pungency commercial grade of ground cayenne pepper (capsicum frutescens), or black pepper (piper nigrum), as an indicator of approximate concentration within each carrier. Their equivalents may be estimated, and prepared from commercially available oleoresin, or from any of the pungent principals, some of which are also available commercially in pure natural, or synthetic form.

The term "pepper", or "pepper compounds" are used somewhat generically to indicate a "pungent botanical". Other botanicals such as those of the Zingiberacea family including ginger (Zingiber officinale), turmeric (Curcuma longa), cardamon (Elettaria cardamomum), Melegueta pepper (Aframonum melegueta), members of the Euphorbia genus including Euphorbia resinifera, poinsetta (Euphorbia pulcherrima), clove (Eugenia aromatica), allspice (Pimenta officinalis) and others having similar constituents may be prepared in the same way as pepper by following the general procedures outlined below in the capsicum pepper illustration below. Included among this list of botanicals is of course the other members of the Solanacea pepper family including members of the capsicum genus with the annuum, baccatum, and longum species. Among the Piperacea family, species of the peperoma, and piper genus which include the retrofractum, nigrum, and longum species. Other species of plants having similar chemistry may also be used in place of the above.

The performance of each preparation will of course depend on type, and concentration of botanical, carrier, and solvent used in relation to the particular pathogenic organism involved. The chemical properties, and solubility of many of these botanical compounds, including information on separation, and quantitation of their constituents are also available from similar sources in the scientific literature, and and may be consulted for more detailed investigations.

For purposes of research, or the treatment of disease, the individual compounds responsible for the pungent quality of red peppers, and other capsicums may be obtained directly from ground red pepper, according to procedures described in the article "Separation and Quantitation of Red Pepper Major Heat Principals by Reverse Phase High-Pressure Liquid Chromatography" by Patrick Hoffman et. al., in the *Journal of Agricultural Food Chemistry* 1983, Vol. 31, pages 1326–1330. Though several related capsaicinoids have been identified in trace amounts, the major capsaicinoids (FIG. 6) include:

Capsaicin. $C_{18}H_{27}NO_3$
(N-[(4-hydroxy-3-methoxyphenyl)methyl]8-methyl-6-nonenamide).
Dihydrocapsaicin. $C_{18}H_{29}NO_3$
(N-[(4-hydroxy-3-methoxyphenyl)methyl]-8-methylnonanamide).
Norcapsaicin. $C_{17}H_{25}NO_3$
(N-[(4-hydroxy-3-methoxyphenyl)methyl]7-methyl-5-octenamide).
Nordihydrocapsaicin. $C_{17}H_{27}NO_3$
(N-[(4-hydroxy-3-methoxyphenyl)methyl]-7-methyloctanamide.
Homocapsaicin. $C_{19}H_{29}NO_3$
(N-[(4-hydroxy-3-methoxyphenyl)methyl]-9-methyl-7-decenamide).
Homodihydrocapsaicin. $C_{19}H_{31}NO_3$
(N-[(4-hydroxy-3-methoxyphenyl)methyl]-9-methyldecanamide).
N-vanillyl-n-nonamide. $C_{17}H_{27}NO_3$
(N-[(4-hydroxy-3-methoxyphenyl)methyl]-n-nonamide).
Nonanoic acid vanillylamide. $C_{17}H_{29}NO_3$
Decanoic acid vanillylamide. $C_{18}H_{31}NO_3$ Other capsaicinoids, not listed here, are identified in research literature as trace elements within capsicum, and may be used in medicinal preparations as well, along with other analagous compounds.

Figure 7:
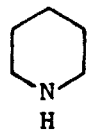

Capsaicinoids may be generally classified as acid amide derivatives of phenol (FIG. 1). The characteristic pungent, irritating sensory effects of these compounds are typical of acid amides, whether derived from phenol, or piperidine (FIG. 7).

Phenol (FIG. 1), though lacking pungent flavor, is highly corrosive, caustic, and toxic, deriving many of its properties from its basic benzene structure. While this gives phenol certain antimicrobial properties, it is generally considered to be unsuitable for therapeutic use in man, and animals, due to it's high toxicity, and irritating effects on tissue.

With the addition of a methoxy goup ($OCH_3$) to phenol, methoxyphenol is formed. In the ortho position, we have ortho-methoxyphenol (FIG. 2), also known as guaiacol, an extract obtainable from trees of the guaiacum genus. The effect of this methoxy group in part is an increase in aromacy, and a decrease in toxicity, and caustic properties otherwise existing in phenol, yet without apparent decrease in antimicrobial properties. The attachment of hydrocarbon groups to the ring structure, to form higher analogues apparently increases the antimicrobial properties of methoxyphenol, and phenol. It is presumed that the meta, or para isomers of methoxyphenol have similar properties to the ortho, in like manner to the similarities between the phenol isomers.

Figure 3:
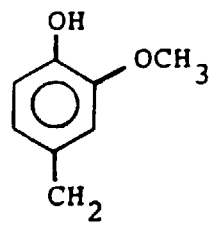

The addition of the methylene group ($CH_2$) in the para position to ortho-methoxyphenol produces vanillyl (FIG. 3). Like phenol, and methoxyphenol, it is presumed that changing the position of the methylene group to form other vanillyl isomers will produce compounds of similar, although not exact properties to that of vanillyl.

The vanillyl structure on which the capsaicinoids are constructed is also typical of the pungent principals found in ginger (zingiberacea) species of plants.

Collectively known as gingerol (FIG. 11): shogaol, paradol, zingerone, gingerol and other analogs, have a different side chain than the capsaicinoids, and lacking an ammonia ($NH_n$) group, are neither amines, or amides like the capsaicinoids or piperidines. Hydrolysis of gingerols yield vanillyl, and a fatty acid side chain, both of which demonstrate like therapeutic properties to the capsaicinoid hydrolytes.

Also members of the ginger, or Zingiberacea family, turmeric (Curcuma longa L.) contains the compound curcumin (FIG. 10), actually a vanillal derivative differing from vanillyl by one hydrogen (H) atom having an (CH) substituent, rather than a methylene ($CH_2$) in the para position. This analog differs further with a side chain unique from the others. Cardamon, allspice, clove, black pepper, and many others contain eugenol, another vanillyl analog with yet another hydrocarbon side chain.

Other botanical sources of vanillyl analogs include gum euphorbium, and extract of certain species of the Euphorbia genus, which contain the capsaicin analog resiniferatoxin (FIG. 12), along with its analog tinyatoxin (FIG. 13) and others.

Figure 5:
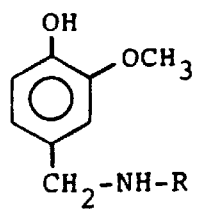

Replacement of one of the hydrogen (H) atoms of ammonia ($NH_3$), with vanillyl, and the replacement of the other hydrogen (H) atom with an organic hydrocarbon group produces vanillylamide (FIG. 5). In the case of the capsaicinoids (FIG. 6), or capsaicin analogs for example, this organic hydrocarbon group is a chain acid (R'), varying from about 8, to 14 carbon atoms, depending upon the particular capsaicinoid. These side chains, both saturated, and unsaturated (including add to the pungency of capsicums, and themselves possess antimicrobial properties of their own, without apparently contributing corrosiveness, or toxicity to vanillylamide.

Hydrolysis of capsaicinoids yield active agents as well. The splitting off of the side acid chain, and it's replacement with a hydrogen (H) atom yields the primary amine vanillylamine, or 3-methoxy-4-hydroxybenzylamine (FIG. 4) from vanillylamide (FIG. 5), in the case of all capsaicinoids. Conversely, the side acid chain, receiving a hydroxy (OH) group, is converted to a fatty acid, and yields a different hydrolyte for each individual capsaicinoid. In the case of capsaicin (FIG. 6), hydrolysis of the side acid chain R' (FIG. 6) CO—$(CH_2)_4$—CH=CH—$(CH_3)_2$ yields iso-decylenic acid COOH—$(CH_2)_4$—CH=CH—CH—$(CH_3)_2$.

The piperidines (FIGS. 7 & 8)), represent a group of analogous alkaloid compounds from which most of the pungent principals found within plants of the piperacea family, of which black pepper (piper nigrum) is a member, are found. Also classified as acid amides, the piperidines, like the capsaicinoids found in capsicum species, are primarily responsible for the characteristic sharp, pungent taste of black pepper.

The piperidine ring (FIG. 7) structure is diverse from that of phenol (FIG. 1). Though also a six membered, carbocyclic compound, piperidines instead contain one nitrogen (N) hetero atom within the ring. Piperidine is heteroparaffinic, and contains no double bonds. The hetero nitrogen atom within the ring is a contributor to the pungency of these compounds. The attachment of a hydrogen (H) atom to the hetero nitrogen atom within the ring forms the amine structure. Attachment of a hydrocarbon group, in the form of a side acid chain (R" FIG. 8) attached to a benzene structure establishes the acid amide structure. These compounds include; piperine $C_{17}H_{19}NO_3$ (FIG. 8), chavicine $C_{17}H_{19}NO_3$, piperettine $C_{19}H_{21}O_3N$, piperidine $(CH_2)_5NH$, piperyline, piperolein A, piperolein B, piperanine, and others.

Hydrolysis of piperidines, like the capsaicinoids, yield active, pungent compounds. Chavicine, for example is hydrolysed to piperidine, which receives an additional hydrogen (H) atom to form a primary amine, and chavicic acid, which receives the hydroxy (OH) group to form the fatty acid.

Hydrolysis of these capsaicinoid, and piperidine acid amides, as well as the other listed compounds may be accomplished with chemical catalysts, or by boiling a liquid preparation of these compounds with water. Hydrolysis does not appear to diminish the pungency of these compounds, and in some cases actually appears to enhance both their pungency, and therapeutic action.

The carbonyl group (C=O) side chain substituent, common to all the above compounds (except eugenol) is also believed to be a contributor to antimicrobial activity.

The chemical structure of prior art antifungals (FIGS. 14–25) use neither the phenolic, or piperidine (FIGS. 7 & 8) amine, or amide structures. The current trend appearing to favor azole derivatives. These include the imidazole (FIG. 19) derivatives such as clotrimazole (FIG. 20), miconazole (FIG. 21), ketoconazole, econazole (FIG. 22), and others. The newer triazole (FIG. 23) class includes fluconazole (FIG. 24), terconazole (FIG. 25), itraconazole, and others.

Other active agents found within capsicum include citric acid, vitamins A, $B_1$, $B_2$, C, and E, iron, potassium and niacin in significant quantities, along with other lipids, and carotenoids including capsanthin, capsorubin, and others. Vitamin C concentrations of 100 milligrams per ounce, are the highest of any natural food compound. Vitamin A content is also high, with 6170 I.U. per ounce.

An infusion of pepper may be prepared by soaking approximately 4 $cm^3$ (¼ teaspoon) of commercially available ground red, or black pepper, to one liter (1 quart) of water of sensibly comfortable temperature. Infusion should be allowed to soak at least ten minutes before use for best results. According to preference, infusion may, or may not be strained to remove plant residue before use.

A tea of is a more potent version of infusion above, using about 16 $cm^3$ (1 teaspoon) of ground pepper for each liter (quart) of sensibly comfortable water. Tea may also be prepared from boiling water, or itself be boiled in water before use. Boiling pepper in water assures complete hydrolysis of the pungent principals, which are also active agents.

A tincture may be prepared by soaking ground red, or black pepper in a solution containing approximately 60% ethanol, and 40% water. Pure ethanol, and other solvents such as acetone, chloroform, vinegar (acetic acid), and others may also be used. The fluid volume of the solution may be about three, or four times that of the dry volume of the ground pepper. The mixture should be agitated, at least occassionally, over a period of at least two hours, with maximum extraction being obtained after about six hours. Allowing the mixture to sit over night produces excellent results. Before use, the residual ground pepper may be strained off, and liquid tincture saved for use.

A preparation of pepper drops may be obtained by reducing tincture through heat, or passive evaporation. Drops made by this method are similar in purity to some grades of commercially available oleoresin of capsicum, and black pepper.

A plaster, or poultice may be prepared by mixing ground pepper with water, until it has a paste-like consistency that will assure good adherence to the skin, or cloth to which it is applied.

A lotion, cream, or shampoo may be obtained by adding to any commercially available shampoo, cream, or lotion, a portion of drops, or tincture equal to approximately 25% of the volume of lotion, cream, or shampoo carrier.

A douche is prepared from infusion, or tea that is strained of the plant residue material before use.

A suppository is made from drops in cocoa butter, or gelatin in the same strength as douche, or lotion.

An injection is prepared from a purified version of infusion, tea, drops, etc., administered intravenously, in tissue, or mixed with, and injected into the spinal fluid.

A powder is pepper in ground form, or extracts mixed, and/or bound within a binding powder carrier such as talc.

Pepper, and any of its active constituents may be administered as a general antiinfective in the treatment of disorders including fungal, and bacterial infections.

Pepper extracts may be administered within conventional drug vehicles, and carriers, and are recommended for use in four basic concentrations. Recommendations for treatment given below are general, and may be altered to suit specific conditions. If one recommended concentration for some reason appears unsuitable, the next graduation should be used.

Other botanicals such as ginger, turmeric, cardamon, clove, poinsetta, ect. which have many therapeutic properties in common with pepper, may be used in place of pepper described below. Though these botanicals share common properties with pepper, variable results between the two are to be expected according to concentration of botanical product, the carrier, and solvent used, and the particular pathogenic organism involved. With this in mind, modifications to the recommendations given below are sometimes warranted depending on specific circumstances. If one recommended concentration is not suitable, a different one may be tried. Factors to consider are the degree of tissue damage, patient sensitivity to the medication, and certainly how anxious the patient is to be rid of the disorder! In most, if not all cases, daily treatment need not be continued beyond the first few weeks to completely resolve dermatophyte infections.

In the lower concentrations, an infusion may be used in the treatment of milder microbial infections including dermatophyte infections, particularly when tissue damage is minimal. Infusion works well as a scalp rinse, a bath for the feet, and skin, and as a douche in the treatment of candida, and other vaginal disorders. Infusion is also recommended if patient sensitivity to the higher concentrations becomes significant.

In higher concentrations, a tincture, a powder, a poultice, and a preparation of drops, are recommended in the treatment of severe dermatophytosis. High concentrates, such as these, are preferred where tissue damage is significant, and where infection sites are causing considerable discomfort for the patient. Drops, for example, work well for topical treatment of nail infections, ringworm lesions, and infected hair. These high concentrates generally produce cure after the first dose when treating skin lesions, and have a prophylactic action of greatest duration, lasting up to about five days after application. As it is usually necessary to induce substantial healing of the skin as a measure against recontamination, and reinfection of dermatophytes, the higher concentrates appear to be most effective as prophylactics as well.

A tea represents a moderate concentration of pepper compounds. It may be used in the same manner as infusion, or in the treatment of more severe cases of dermatophytosis. Tea should be used if infusion fails to bring immediate relief of secondary symptoms, such as itching in athlete's foot, candida, or jock itch, within one hour of the first treatment.

Tea may also be used in place of the higher concentration carriers, such as drops or tincture. It is often equally effective in curing severe cases of dermatophytosis, in which there is significant tissue damage, as the high concentrates. In this case, tea is preferred over the high concentrates, particularly if the patient sensitivity to the medication is causing significant discomfort.

Tea is also suitable as a gargle, or mouth rinse for thrush, or other fungal infections of the throat, and oral cavity.

For an injection of pepper compounds in deep tissue, spinal fluid, or intravenously, milder concentrations, such as infusion are recommended for initial treatment. While injection of pepper extracts such as capsaicin have been administered safely in animal testing of analgesics, it is not known at this writing if data exists on treating humans with injection of pepper compounds.

A lotion, or shampoo may be prepared with any commonly available lotion, or shampoo, and applied to infected areas in its intended manner. Other therapeutic agents, in addition to pepper extracts, may be added to shampoo and lotion. If irritation is a concern, a topical anesthetic, such as lidocaine, or benzocaine may be added to lotion to reduce severity. If skin is very dry, emollients may also be added to lotion.

A pepper aerosol may be inhaled in the treatment of throat, and respiratory infections. In this administration, aerosol should be derived from a lower concentration such as infusion, as pepper is extremely irritating to the nose, throat, lungs, and eyes, especially when airborne. This is especially true of capsicum aerosol. For this reason, aerosol is somewhat limited in it's medicinal application.

The irritating effects of pepper aerosol, and particularly capsaicum, is greater when distributed within an etheric tincture solution, such as alcohol, ether, chloroform, or acetone. Once airborne, even minute concentrations have a tear gas, or macelike effect on the eyes, and respiratory system. A single, half second spray of a cayenne pepper ethanol tincture (60% ethanol/40% water works well) aerosol from a hand held dispenser is sufficient to render a fifteen hundred square foot enclosed area uninhabitable to humans, and animals, as choking, coughing, and burning irritation to the eyes and respiratory system make habitation of the room intolerable.

While this may limit the use of aerosol for medicinal applications, it appears to have tremendous potential for military, and paramilitary applications, particularly as a safe and more effective alternative to tear gas, and other antipersonnel aerosols. Pepper aerosol also show great potential in agriculture as a crop antiinfective/antifungal, insecticide, and pest repellent.

Pepper powder is also very irritating when airborne, and like aerosol, has a more limited medical application than the other carriers. If used as a foot powder for example, it is best to fix the pepper compounds within a powder binder such as talc, to prevent, or lessen escape of airborn particulate.

As to the therapeutic properties of pepper compounds, and are several actions I believe to be at work in the operation of the medication of the current invention. While some of the actions described below are factual, others are theoretical, or hypothetical, and are set forth as possibilities, and are not intended to be binding. They represent an attempt to further explain the operation of the current invention, and to give direction to areas warranting further research.

The first therapeutic action of pepper extracts upon administration is that of an irritant, or as I prefer to call an inflamatory. The irritant constituents of capsicum, namely the capsaicinoids (FIG. 6), their hydrolytes, and the other acid amide piperidines (FIGS. 7 & 8), and their hydrolytes found in black pepper, and related compounds are all instrumental in precipitating a rapid inflamatory response in the area of administration. This is observed, for example, when applied to skin in the treatment of various forms of tinea. The area of treatment often turns red, or pink, and feels warm or hot. Burning, or warm tingling is sometimes reported by patients after topical administration of pepper extracts, usually the result of excessive dosage, or exposure to open cuts in tissue. Though this burning sensation can become quite intense, it does not usually last beyond the first five or ten minutes after treatment. The burning subsides into a warm, tingling sensation that is no longer uncomfortable to patients. The induction of inflammation to the point of pain is accidental, and not necessary for cure. Inflammatory responses associated with even slight warmth and redness are more than adequate to provide sufficient therapeutic action.

The therapeutic value of inflammation, is the stimulation of the body's own immune response in the area of infection. This precipitates a varied array of fungistatic serums, including leukocytes, and other mononuclear cells in the area of infection. These fungistatic serums inhibit the growth of pathogenic fungi.

Inflamation also increases the rate of skin shedding, which combats penetration of the fungus, or other organism into the skin. In this mode of action, the microbe is essentially "cast off" with the diseased tissue. Perhaps or this reason, those varieties of dermatophytosis that are accompanied by inflammation often eventually heal on their own. The noninflammatory varieties such as dry athlete's foot, however become chronic, and are very difficult to heal. The lack of participation of the immune responses of the host prevents healing, and cure.

Pepper compounds are believed to act as an adjuvant to these fungistatic serums, by facilitating their pathways through the blood vessels, and skin of the host, and through the cell wall of the fungi, or other pathogen. Being composed primarily of lipids, capsicum for example is believed to increase the permeability of the cellular membrane of both the host, and fungi. In addition to aiding the delivery of antifungal serum, the increase in cell membrane permeability also facilitates the delivery of undecylenic acid, another antifungal compound found in sweat, into the fungi. With the aid of increased permeability provided by pepper compounds, these antifungal compounds, which are normally fungistatic, become fungicidal.

The direct antimicrobial properties of pepper and another of the notably pungent botanicals ginger may be observed in vitro, in addition to those observed in vivo in the actual treatment of disease.

A series of in vitro tests are conducted on 3 tincture samples prepared from the ground spice of cayenne pepper (Sample A), black pepper (Sample B), and ginger (Sample C). Each spice is measured, and mixed with pure ethanol in an amount three times the measured volume. The mixtures are stored for 18 hours at room temperature (22° C.), and agitated on 5 separate occassions over the period. The mixtures are then strained of residue, and submitted for testing. Also included is Sample F; a tincture prepared with commercially pure capsaicin (8-methyl-N-vanillyl-6-nonenamide) at a concentration of 25 mg./ml. pure ethanol.

Initial in vitro tests performed by a medical university laboratory report that none of the Samples A, B, C, or F show antimicrobial activity against *Candida albicans*, or *Neurospora crassia* on a solid medium, carrot juice agar (pH 6) screening. A liquid assay in vitro screen performed by a major U.S. pharmaceutical company however, reveals activity against all 11 strains of pathogenic fungi tested, including 7 strains of Candida! These pathogenic strains are responsible for deep tissue mycotic infection, although the Candida strains also cause superficial mycotic infections of the skin, and mucosa as well.

At first glance, a general hierarchy of activity relative to the degree of pungency among the botanical Samples A, B, & C is evident, with cayenne pepper being most pungent, followed by black pepper, and then ginger. Though exceptions are evident in the tests, degree of pungency is an accurate general "rule of thumb" with regard to evaluating the relative effectiveness of the botanicals. This observation however, for reasons set forth below, should not be interpreted as an indication that the therapeutic effects of the botanicals are determined solely by the degree, and quantity of pungent principals present in the Samples, though it is a factor. This will be further addressed below.

Perhaps most intriguing of the test results below is that Samples A, B, C, & F of the current invention show greatest activity against those fungal strains most resistant to the drug standard Amphotericin B! In particular, *C. albicans* ATCC 38247, *C. kefyr* ATCC 28838, and *T. glabrata* ATCC 15545 show particular sensitivity to Samples A, B, C, & F in this screen. These strains, being most resistant to standard drug therapies, pose the greatest potential for causing life threatening illnesses. The necessity of prolonged treatment with high dosages of highly toxic antifungal drugs required to treat these diseases is often itself life threatening to the patient.

Another important feature of these test findings is evidence of the presence of multiple antimicrobial compounds within the Samples. In comparing Samples A & F for example, it is apparent that the antimicrobial action of cayenne pepper (Sample A) cannot be wholly attributed to the presence of capsaicin alone in the ground spice.

A review of the aforementioned article "Separation and Quantitation of Red Pepper Major Heat Principals by Reverse Phase High Pressure Liquid Chromatograph" indicates by rigorous testing a total "capsaicinoid" content not exceeding about 1.9 mg./gram in common red pepper. Sample A being diluted 3 times with ethanol would fix its maximum capsaicinoid content at perhaps 0.063%, or about 630 ug./ml. Capsaicin accounting for about half of the total capsaicinoid content of common red pepper, would fix the capsaicin content of Sample A at about 0.032%, or about 320 ug/ml. This diluted 256 times shows Sample A as having activity against *C. albicans* ATCC 38247 at a capsaicin concentration of less than 1.25 ug./ml., and total capsaicinoid content of less than 2.5 ug./ml against which Amphotericin B requires a concentration of 25 ug/ml.! Additionally, capsaicin though the most toxic compound found in any significant amount in capsicum peppers, is much less toxic than Amphotericin B!

In comparison, Sample F has a concentration of pure capsaicin at 25 mg./ml.–about 40 times the total capsaicinoid content of Sample A, yet is still short of the Sample A performance accross the board! This can only mean the presence of another antifungal compound, and/or a synergistic relationship between the mix of capsaicinoids and other compounds within the botanical that account for the total antimicrobial effect. It may also suggest that the therapeutic actions of these botanicals are not generally improved by extensive isolation of their individual constituents, and that the total therapeutic mechanisms involved are quite complex, involving a substantial number of compounds in addition to the phenols, and piperidines present. In this respect, high purification of individual constituents has the undesireable effect of to some degree dismantling the full therapeutic action of the compound.

Sample F is the exception containing a purified isolate (capsaicin) of the primary pungent principal found in red pepper and other capsicums. Sample F also has perhaps 3 times the capsaicinoid, and 6 times the capsaicin content of the most pungent species of capsicum known to exist in nature. Yet accross the board, Sample F falls short of the basic botanical extract Sample A even though it has 40 times the capsaicinoid concentration of Sample A!

While the above tests provide important insight into some of the therapeutic actions of the current invention, they are of course only partially indicative of the full antimicrobial action present, even as the earlier carrot juice agar tests failed to reveal any activity at all. The fuller antimicrobial activity of the compounds described above are of course observed in vivo in the actual treatment of disease, wherein the bodily immune responses are also modulated. These compounds repeatidly cure dermatophyte infections in as few as a single application. Can this be said of Amphotericin B, or any of the other currently available topical treatments? Absolutely not!

| | Minimum Inhibitory Concentration | | | | |
|---|---|---|---|---|---|
| | test sample (number of dilutions) | | | | standard µg/ml |
| Organism | A | B | C | F | Amphoter.B |
| Candida Albicans ATCC 10231 | 16 | 16 | 8 | 8 | 1.56 |
| Candida Albicans 579a | 16 | 16 | 8 | 8 | 1.56 |
| Candida Albicans 442 | 16 | 16 | 16 | 16 | 1.56 |
| Candida Albicans ATCC 38247 | 256 | 16 | 8 | 256 | 25.00 |
| Candida Albicans ATCC 62376 | 16 | 16 | 8 | 8 | 1.56 |
| Candida tropicalis NRRL-Y-112 | 16 | 32 | 16 | 16 | 1.56 |
| Candida kefyr ATCC 28838 | 64 | 32 | 16 | 16 | 3.12 |
| Torulopsis glabrata ATCC 15545 | 16 | 32 | 16 | 8 | 3.12 |
| Cryptococcus albidus ATCC 34140 | 4 | 8 | 8 | 16 | 1.56 |
| Saccharomyces cerevisiae GSI-36 | 16 | 16 | 8 | 16 | 1.56 |
| Aspergillus niger ATCC 16404 | 16 | 4 | 4 | 4 | 1.56 |

Spec: Yeast extract Nitrate Broth + Glucose, water solvent, 48 hour Incubation, all Samples precipitate at 50% in YNB + G.
Sample A = cayenne pepper*
Sample B = black pepper*
Sample C = ginger*
Sample F = capsaicin
(commercially pure 8-methyl-N-vanillyl-6-nonenamide) 25 mg/ml pure ethanol.
*tinture 3:1 ground spice and ethanol 18 hours @ 22° C.

The irritant acid amides found within both kinds of pepper, and their hydrolytes, appear to have direct fungicidal actions. Isodecylenic acid, one of the hydrolytes of capsaicin, is believed to have antifungal properties superior to it's fatty acid chain relative, undecylenic acid, and offers important clues to the developement of still other antimicrobials, structured similarly for increased effectiveness. Another hydrolyte of the capsaicinoids, 3-methoxy-4-hydroxybenzylamine (FIG. 4), suggests a new class of amine antimicrobial compounds, derived from this, and other analogus structures.

Other possible antimicrobial agents found in pepper plants, that may play a role in producing curative results, are known as phytoalexins. Phytoalexins, such as the compound capsidiol, found in plants of the solanacea family which includes capsicums, are a group of antimcrobial agents, not normally present in the plant, that are produced by the plant, only in response to trama caused by heat, cold, mechanical injury, or attack by insects, or microbes. Capsidiol, and other of the phytoalexins produced by solanacea species, are known to have antifungal properties against fungi that are pathogenic to solanacea species of plants. While these fungi are not patogenic to man, it is possible that capsidiol, or another phytoalexin produced in response to their challenge, has antifungal action against fungi that are pathogenic to man, as well as those pathogenic to plants. It is therefore possible that capsidiol, or another phytoalexin may play a role in curing fungal disorders in man and animals, as well as plants.

Dehydration is another possible therapeutic action of pepper compounds. In the treatment of superficial mycoses, pepper extracts appear to dry the skin to a degree that may be inhospitable to fungi. Perhaps the result of increased permeability, or the formation of salts on the skin, the skin, though drier, is not uncomfortably so, and may have at least a fungistatic effect as a result of reduced hydration.

The prophylactic action of pepper extracts is another important therapeutic feature of the current invention. In addition to having immediate fungicidal action in the treatment of superficial mycoses, pepper compounds remain in the skin for perhaps ten days after treatment, to prevent reinfection. Patients often report the reoccurrence of the warm, tingling sensation in treated areas while bathing, days after treatment. Exposure to water appears to also restimulate its therapeutic action as well. If feet, or skin become moist, and sweaty, the therapeutic action is intensified, at the same pathogenic fungi would otherwise proliferate. This provides a shield against reinfection due to recontamination, and protects the skin while it heals.

Pepper compounds also function as a vulnerary, aiding, and accelerating the healing and regeneration of tissue. As tissue damage can be severe in certain forms of dermatophytosis, such as favus, nail infections, and athlete's foot, it becomes necessary to heal the damaged tissue before full cure is possible. Pathogenic fungi, finding opportunity in damaged skin for example, will often continue to reinfect those areas unless the skin is healed. This is one reason prior art medications are so ineffective towards cure. It becomes necessary to heal the skin to safeguard against repeat infection, as healthy, whole skin is the best protection against reinfection. As capsicum for example, is particularly high in vitamins, and other nutrients, they also appear to have a healing effect on damaged tissue.

The power of pepper compounds to excellerate healing of injured tissue is also quite dramatically demonstrated in the treatment of lacerations. We commonly have treated the most stubborn, long lasting laceration infections with pepper compounds (lotion containing hydrolysed black pepper drops is a personal favorite), only to witness within just hours, reductions in redness, swelling, sensitivity, and exudate that are quite frankly hard to believe! One is equally astounding upon witnessing the improvement seen in just a day or two after treatment!

A medication such as described above is an invaluable wound healing treatment, particularly for the immune suppressed, and should be used to treat cancers, and other neoplasms.

Pepper compounds are also unbelieveably effective in the treatment of burns, and abrasions. On several occassions I have treated burns with pepper lotion with results as astounding as with lacerations. The improvement in the healing of the skin is quite notable within hours, with continued improvement in the following days that is nothing short of astounding. This also is very important to burn patients, and is likely to excellerate recovery to a degree that will save the lives of many that would otherwise die from their injuries.

Pepper compounds could be injected into deep tissue to excellerate the healing of buises and contusions. This would be of great benefit to athletes, and accident victims.

Other antimicrobial actions of pepper compounds are perhaps due to the high concentration of antioxidant compounds such as vitamin E, aromatic amines, phenols, and amino phenols found in pepper, particularly capsicum. These antioxidants may interfere with the action of digestive enzymes secreted by the fungi, that are necessary for ingestion of nutrition, in effect starving the fungi. It is also possible that high concentrations of citric acid, or vitimins found in pepper, are directly toxic to the fungi.

Conversely, the very high concentration of vitamin C, a known oxidant, may also interfer with the ability of the fungi to digest, and ingest nutrition, by instead oxidizing it's food compounds before they can be absorbed, also depriving the fungi of food.

Since capsicum is so high in vitamin A, the B complex, C, D, and E, it can be used to treat several nutritional disorders including scurvy, pellagra, beriberi, rickets, xerophthalmia, and a host of related diseases. Significant amounts of iron, and potassium, make it excellent for correcting fluid absorption, and retention imbalances that result from dehydration due to diarrhea, and vomiting. Infusion, or tea of capsicum may be given to correct dehydration due to diarrhea. Soaking the ground powder only briefly in cool water, to produce a cold tea, or infusion should be sufficient to release the water soluble C, and B vitamins, and mineral salts, without releasing as many of the pungent principals, which may make ingestion difficult.

Other evidence of the healing, and regenerative properties of pepper is observed in the treatment of other skin diseases such as psoriasis, dandruff, seborrhea, and other forms of eczema. Topical treatment of these disorders with pepper, within the same drug vehicles and carriers described here in the treatment of fungal disorders, produces curative results that are equally astounding. As these diseases are not believed to be of microbial origin, they are none the less completely healed, usually without relapse, after as few as one single treatment! This is further evident that pepper compounds stimulate the healing process of the skin, and encourage regeneration, growth, and normalization of tissue function.

Pepper compounds also appear to possess keratolytic actions, which aid healing of these general forms of dermatitis, by aiding in the breakdown of keratin in the skin. This also makes them useful in the treatment of warts, corns, callouses, acne, wrinkles, and cancers. Keratolytic action may also have an antimicrobial effect, by perhaps interfering with the ability of pathogenic microorganisms such as fungi to digest, or ingest the keratin on which they feed.

In one study, a four year old girl, with chronic seborrhea of the scalp, was completely healed of the disorder after just three treatments with capsicum drops. The girl has two lesions, approximately 25 mm (1") diameter on the top portion of her scalp, that she has had since infancy. The lesions are tightly packed with thick, yellowish white scales approximately 2 mm ($\frac{1}{16}$") in diameter. The area above the lesions is covered with loose scales, that are seen whenever the hair is parted.

The two seborrhea lesions are treated topically, with capsicum drops, prepared from heat evaporated tincture. The dosage is once a day for three consecutive days.

Within the first few weeks, the lesions gradually lose their superficial loose scales, leaving only the tightly packed scales that are the lesion itself. At three weeks, however, even the tightly packed scales have disappeared, and no lesions can be found; the patient is completely healed! The area of scalp previously infected with seborrhea is now healthy, and normal, and completely indistinguishable from the rest of the scalp, which is healthy. It is not possible to determine if the girl had ever even had seborrhea, as no evidence of the prior disease can be found on very close examination. Subsequent examinations over a period of several months indicate a healthy scalp, with no recurrence of seborrhea or any other dermatologic disorder.

Another illustration of the keratolytic properties of pepper compounds involves a 12 year old boy, afflicted with a large plantar wart on the heel of his foot, in which the boy is completely healed after a single treatment with a pepper extract.

The boy has a large, brownish colored plantar wart on the upper inside portion of the heel of his right foot. For more than two years, the wart has caused the boy mild, to extreme discomfort, particularly when walking. On numerous occassions over the course of this period, the wart has been treated with several over the counter, and physician prescribed topical medications that yield no noticable improvement in the condition. The boy is accustomed to shaving the wart off at the skin surface at regular intervals to reduce the size, and hence the degree of discomfort associated with its rapid growth. When the upper layers of the wart are removed in this manner, the remainder of the tumor appears as a cluster of milky-white stones buried below the translucent layers of skin on the heel. Regardless of these continued treatments, the wart continues to grow back causing the usual discomfort.

Prior to treatment with pepper drops, the wart is examined, and appears to occupy a brownish, rough area of the heal approximately 25 mm. (1") in diameter at the base. The central portion is raised, forming a nodule approximately 6 mm. ($\frac{1}{4}$") above the skin surface.

The wart is treated topically with one (1) drop of pepper drops that were prepared from a standard 4:1 red pepper acetone tincture that was reduced 40 times by room temperature evaporation. Upon application, the boy reports no notable sensation from the treatment.

Eight weeks after this single treatment, the boy's heel is again examined, and to the astonishment of the boy and his mother the wart is completely disappeared! Close examination of the entire foot shows no evidence of warts. The previously infected area of skin looks perfectly normal and healed, with no trace of disease, or abnormality.

When asked about details of the course of healing of the wart, the boy replied that after treatment with the pepper drops, he had experienced no further discomfort in the area of the wart. This lack of discomfort caused him to forget about the wart, and he had not looked at it since treatment.

The above illustration in addition to demonstrating the keratolytic activity of pepper compounds also suggest the possibility of antimicrobial activity. Viruses being a known cause of warts are probably inhibited by pepper compounds. This in combination with the keratolytic, and perhaps vulnerary action of pepper are responsible for such dramatic healing results. It has been many months at this writing since the boy's treatment. The wart has not returned, nor have new ones arisen.

From these examples, we see the multiple therapeutic actions of pepper, its constituents, and related compounds for stimulating healing, and regeneration of tissue damaged by both disease, and injury, in addition to its antiinfective uses, and how pepper appears to interact with the body's own regenerative capabilities to normalize health, and function of tissue. Many other examples exist which illustrate these same therapeutic actions at work in the treatment of diseases that cause abnormal growth, and proliferation of keratin including eczema, general dermatitis, and practically all other dermatologic disorders.

Industrial Applicability

Thus the reader will see, that the current invention provides an antimicrobial treatment, with a degree of effectiveness in the treatment of fungal diseases that is many generations ahead of the prior art.

Naturally occuring compounds, found in pepper plant species of the solanacea family, which include the capsicums *C. frutescens, C. annuum, C. Baccatum*, and the piperacea family which includes the peperoma, and piper genera, and the well known retrofractum, nigrum, and longum species among others, and related compounds, are found to have profound therapeutic actions in the treatment of fungal disorders. These compounds may be administered in most commonly used drug delivery vehicles, and carriers, with outstanding results.

A single topical treatment with my medication is all that is usually necessary to provide complete cure for most superficial mycoses including ringworm, inflamatory athlete's foot, jock itch and candida. The onset of effect is immediate, with cessation of symptoms usually within the first hour of treatment, and complete healing within the first few days.

Prior art topical medications, on the other hand, usually require scores of applications before full results are seen, and often do not provide adequate cure, much less relief of symptoms even with long term use.

Even recalcitrant cases of dry athlete's foot, which often require months of treatment with prior art systemics, is completely healed usually within less than a dozen topical treatments with my medicine. Severe cases of dermatophytosis such as this, and others, may now be treated topically by the sufferer, with a relative few applications of an over the counter treatment containing pepper extracts.

Prior art systemic treatments, which require the attendance of a dermatologist, and daily multiple doses of the medication over a period of several months, can cost hundreds of dollars to treat, and are often unsuccessful in providing complete cure. In addition to this considerable cost in time, money, and inconvenience, prior art systemic antifungals have many adverse effects, which are not only unpleasant, but can themselves cause serious health problems. The risk of damage to internal organs, blood composition and adverse interactions with other medications, are factors that must be carefully weighed by physicians administering prior art systemic antifungals. With this, other less sever, yet unpleasant side effects include nausea, vomiting, headache, dizziness, fever, diarrhea, and many other disorders that contribute to the misery and ill health of the patient.

With pepper compounds, systemic treatment with prior art antifungals, with their high cost, weak therapeutic action, and adverse side effects are no longer necessary to treat superficial mycoses. Instead of months of systemic therapy that is very costly, time consuming, slow to provide results, and an endangerment to health, the sufferer can cure the condition themselves, with a safe, inexpensive, and astonishingly powerful medicine such as mine.

Pepper compounds are safe, being a food, consumed by man for thousands of years, and do not induce illness in the patient as prior art antifungals often do. Pepper is widespread throughout the world, and is grown in virtually every country. Its active constituents, most of which are pungent acid amide compounds, easily obtainable from the ground product, have all been synthesized, and many are available from commercial drug and chemical manufacturers.

The amazing healing power of my medicine, coupled with the tremendous economic advantage it provides, paves the way for the creation of many new and very large markets for topical treatment of dermatophytosis. Rather than exclude the economically disadvantaged from treatment, as prior art antifungal do because of their high cost, and meager effectiveness, my treatment can be produced, and sold for less than prior art topicals, and still provide a larger profit margin for marketers than is common within that industry. My product will greatly expand the market base for tinea medicines alone by tens of millions of individuals worldwide, and most importantly, provide effective medical care for those most in need of it.

Even severe cases of dermatophytosis, which cost hundreds of dollars to treat with prior art antifungals, can be completely cured in less time, and for less than one cent worth of pepper. A product such as this, sold for just one dollar, will attract many millions of consumers to the market, who are currently excluded because of the high cost and ineffectiveness of currently available prior art topical antifungals.

The high effectiveness, low toxicity, and very low cost of My medication will greatly broaden the size of the veterinary market for treatment of mycoses. The high effectiveness, low toxicity, and very low cost of my medicine also makes feasible the creation of a significant market for treatment of mycoses within the livestock industry. Being highly contagious, and finding opportunity under certain common weather conditions, dermatophytoses such as ringworm for example, can become epidemic within a herd, within a very short time, disqualifying them from sale at the feed lots.

The weak therapeutic action, and high cost of prior art topical antifungals has prevented the formation of a market for the treatment of livestock for superficial mycoses. To treat food animals such as cattle, with any of the prior art topical antifungals before market is an absurd notion. The cost of medicine, its very slow action, coupled with the very considerable amount of labor required to repeatedly administer the medicine, can never be justified from an economic standpoint. For this reason, no significant market exists within the livestock industry for such products.

With the treatment of the current invention, however, the combination of safety, low cost, and astonishing effectiveness, make it now economically feasible to establish a product for treatment of ringworm, candida, and other superficial mycoses within the livestock industry, as well as for deep tissue microbial infections. Being derived from food compounds generally recognized as safe (GRAS) by the U.S. Food and Drug Administration, my medication is especially appropriate for use in the livestock industry. With my medication, an outbreak of ringworm within a herd, in the last week before market, need no longer prevent them from market as before. In addition to topical application, analogs of pepper's active agents may be added to livestock feed to prevent systemic diseases as well.

Pepper, and it's active constituents provide an important research tool in the treatment of deep tissue fungal disorders, as well as the superficial varieties. The almost universal interchangeability of antifungal medications, between topical and systemic adminsitration, suggests the use of pepper compounds for systemic, as well as topical use in the treatment of deep tissue mycoses. Pepper extracts may be given by injection into the blood, spinal fluid, or directly into diseased tissue for the treatment of aspergillosis, actinomycosis, crytococcocis, entomophthoromycosis, histoplasmosis, blastomycosis, coccidioidomycoses, paracoccidioidomycoses, candidiaisis, and other deep tissue fungal disorders. Analogs of pepper's active constituent may also be developed for oral administration to prevent decomposition as a result of digestive processes.

With the very rapid increase in the incidence of deep tissue fungal disorders, and projections suggesting even greater incidence in the future, the need for safer, more powerful treatments is more crucial than ever. Finding opportunity in immunocomprimised patients such as organ transplant patients, and others on immunosuppressant drugs, and those suffering from AIDS; these diseases are life threatening.

Also life threatening to immunocomprimised patients, is treatment with prior art antifungals. Their high toxicity, and multiple adverse side effects often have devastating impact on the health of these patients, who are already very sick. Complications from these adverse effects can well end their lives, in addition to adding extra misery to their already tragic circumstances. The risk of damage to internal organs, changes in blood composition, and adverse interactions with other medications, along with the nausea, vomiting, diarrhea, headache, fever, and other adverse effects associated with prior art systemic treatment, is extremely unlikely occur with pepper extracts. In this way, pepper compounds will not add illness to illness, but healing to the patient, without discomfort, or injurious side effects.

Pepper's ability to induce an inflamatory response in the area of administration provides an important research tool for studying immunostimulation in the treatment of disease. Since inflamation precipitates a varied array of antifungal serums, including leukocytes, and other mononuclear cells to the site of infection, this antimicrobial effect is believed to play a major role in pepper's astounding success at curing microbial infections of the keratin layers. These properties are valuable in the systemic treatment of disease as well, and particularly so for immunocomprimised patients.

Perhaps other notably pungent compounds such as those found in garlic, onion, mustard, vanilla, cascarilla, nicotine, lobeline, boneset, etc., also demonstrate similar therapeutic actions as those found in pepper. It is also probable that nearly all irritants, whether natural, or synthetic, possess to some degree these same general properties, and aid cure through induction of inflammation.

The role that the active principles in pepper play in the amazingly rapid healing, and regeneration of tissue injured by burns, lacerations, infections, and disease is also important to immunocomprimised patients, who have particular difficulty in healing, and frequently encounter serious infection from even minor injuries, and diseases. These vulnerary actions also play an important role in the treatment of cancers, and tumors, and other diseases that result in cellular mutation, and abnormal proliferation of tissue.

The astounding effectiveness of pepper compounds to cure dandruff and seborrhea further suggests its regenerative contributions, in addition to its antifungal actions. Though not believed to be of microbial origin, dandruff and seborrhea are completely cured within a very few topical treatments with pepper, as easily as if it were ringworm. These healing and regenerative powers, along with pepper's apparent keratolytic action, also provides great promise in the treatment of all diseases that result in an abnormal proliferation of keratin including scaling conditions such as eczema, psoriasis, general dermatitis, or hardened growths such as warts, corns, and callouses, ect. These properties also make pepper useful in treating cancer, wrinkles, acne, and others disorders.

The discovery of pepper's amazing effectiveness in the treatment of dandruff and seborrhea, also suggests that other antifungals, including those of the prior art, may also demonstrate effectiveness in the treatment of these, and other forms of dermatitis.

The antimicrobial actions of pepper extracts towards pathogenic fungi, make it an excellent prospect for experimentation with other pathogens such as bacteria, in the development of new antiseptics and antibiotics. Pepper's affinity for the skin also makes it a good candidate for the treatment of staphylococcus, and other bacterial infections of the skin. It's low toxicity also favors its use in the treatment of systemic bacterial infections including all types from ear infections to tuberculosis.

Other products utilizing the antimicrobial properties of pepper compounds include clothing, and shoe liners made from capsicum wool, or any other fabric impregnated with pepper compounds as a safeguard against harboring these pathogens within one's clothing. For individuals who, for example, have a natural proclivity for contracting athlete's foot, socks, or shoes with liners impregnated with pepper may be worn to prevent contamination leading to infection. The same applies to undergarments, and athletic wear, or anything that has contact with the skin, and is a potential contagion of infection.

Pepper offers promise in a wide variety of agricultural applications as well. Crop fields may be sprayed or dusted with pepper preparations, or added to irrigation water to facilitate a variety of important operation. The antimicrobial properties of pepper will protect the plant from fungal, bacterial, and viral disease. It will also protect harvested produce from spoilage. In these two respects, crop yield is increased, and allowable storage time extended, as microbes take a far less significant tole of the harvested crop.

Pepper's action as an irritant, further serves increased crop yields by performing as a repellent for crop destroying animals and insects, in addition to acting as an insecticide. In aerosol form, capsicum preparations in particular perform like mace, or tear gas, producing extreme burning and irritation of the eyes, nose throat, lungs, and all mucous membranes in amazingly low concentrations. Crops in fields treated with capsicum and related plant species will have an intolerably offensive taste and odor, that will repel rodents, birds, insects, and microbes that otherwise damage crops. Within storage silos, pepper preparations will act as a preservative by continuing to stem these destructive influences, even after delivery to market.

The irritating constituents of pepper are also useful for military and law enforcement purposes, as safe alternatives to mace and tear gas, in addition to their therapeutic, and agricultural uses. When dispersed in a fine mist, or vapor containing an etheral solvent such as alcohol, capsicum pepper in particular produces extreme, and intolerable irritation to the eyes, and respiratory system, along with uncontrolable choking, and coughing in the most minute dosages! An invisible, and odorless vapor containing a single squirt from a typical fine mist cosmetic bottle containing cayenne pepper ethanol tincture is sufficient to render a fifteen hundred square foot room uninhabitable to humans. Dispersed within tear gas-like canisters, specially suited for the purpose, very large areas of atmosphere could be covered with very few distribution units.

Pepper derivatives, whether used to treat crops, or livestock, are perfect for use in the food industry. Being itself a food compound, generally recognized as safe (GRAS) by the U.S. Food and Drug Administration, pepper will pose no health risks to consumers of these food products. Whether applied topically to livestock, or added to their feed, or injected as a systemic antibiotic, pepper derivatives will not raise crucial safety concerns, as all prior art systemics have.

Other possible areas for investigating pepper and its derivatives include treatment of trees for Dutch elm disease, and other disorders, and treatment of rare painting and artifacts as a preservative, and as disinfectant, and as a treatment against parasitic worms.

The list of possible research projects, for the development of new commercial product derived from the discovery of pepper's absolutely astonding curative powers, is indeed endless. What new products that are to develop from this discovery is an interesting, and exciting area deserving of much attention.

The use of pepper compounds in the treatment of tumors, cancer, and other diseases involving cellular mutation of tissue, along with immune disorders such as AIDS, has excellent prospects for the developement of many new drugs, and treatments.

The impact of commercial implementation of this topical antifungal treatment alone, is to make available to even the poorest people of the world a certain cure for even the most severe cases of superficial mycoses. A treatment that cures completely in much less time, in a much safer way, and for less than one penny on the dollar for what is required with prior art treatments. A medication that brings relief to many millions of sufferers, rich and poor, saves our nation, and each nation of the world millions of dollars each day in medical costs. A medicine that provides an important search tool in the treatment of deep tissue mycoses, her life threatening infectious diseases.

While my above description includes many specificities, these should not be regarded as limitations on the invention, but rather as an exemplification of certain preferred embodiments.

Accordingly, the scope of the invention should not be determined by these illustrated embodiments, but by the appended claims, and their legal equivalents.

I claim:

1. A method of treating deep tissue, or systemic fungal diseases comprising:

administration to an area of disease a suitable carrier containing a primary anti-infective agent obtainable from capsicum pepper, or an equivalent in a therapeutically effective amount.

2. A method of treating systemic fungal diseases selected from the group consisting of blastomycosis, coccidioidomycosis, entomophthoromycosis, or paracoccidioidomycosis comprising:

administration to an area of disease a suitable carrier containing a primary anti-infective agent obtainable from pepper, or an equivalent in a therapeutically effective amount.

3. A method of treating systemic fungal diseases selected from the group consisting of aspergillosis, candidiasis, cryptococcosis, or histoplasmosis comprising:

systemic administration to an area of disease a suitable carrier containing a primary anti-infective agent obtainable from pepper, or an equivalent in a therapeutically effective amount.

4. A method of treating fungal infections of the mucosa comprising:

administration to an area of disease a suitable carrier containing a primary anti-infective agent obtainable from a pepper plant of the genus Capsicum, Peperoma, or species Piper retrofractum, Piper longum, or Piper nigrum in a therapeutically effective amount.

5. A method of treating the superficial manifestations of fungal disease in the areas of the body about the face, ear, mouth, neck, and below and deep tissue, or systemic fungal diseases comprising: administration to the area of disease a suitable carrier containing a primary anti-infective agent obtainable from pepper, or an equivalent wherein a therapeutically effective amount is a concentration similar to oleoresin or less.

6. A method of treating the superficial manifestations of fungal disease or systemic fungal diseases comprising:

administration to the area of disease a suitable carrier containing a primary anti-infective agent obtainable from pepper, or an equivalent wherein a therapeutically effective amount is a concentration within the range of ground spice or oleoresin.

7. A method as in any one of claims 5 or 6, wherein the disease infects the feet.

8. A method as in any one of claims 5 or 6, wherein the disease infects the body area.

9. A method as in any one of claims 5 or 6, wherein the disease infects the crotch area.

10. The method of claim 6, wherein the disease infects the scalp.

11. A method as in any one of claims 1–6, wherein the disease is candidiasis.

12. A method as in any one of claims 1–6, wherein said agent is a synthetic.

13. A method as in any one of claims 2, 3, 5, or 6, wherein said pepper is a Capsicum.

14. A method as in any one of claims 1–6, wherein said agent is a capsaicinoid analog.

15. A method as in any one of claims 2, 3, 5, or 6, wherein said plant is piperaceous.

16. A method as in any one of claims 2, 3, 5, or 6, wherein said agent contains a piperidine constituent.

17. A method as in any one of claims 1–6, wherein said pepper is cayenne.

18. A method as in any one of claims 1–6, wherein said pepper is paprika.

19. A method as in any one of claims 1–6, wherein said pepper is black.

* * * * *

UNITED STATES PATENT AND TRADEMARK OFFICE
CERTIFICATE OF CORRECTION

PATENT NO. : 6,063,381
DATED : May 16, 2000
INVENTOR(S) : Staggs

It is certified that error appears in the above-identified patent and that said Letters Patent is hereby corrected as shown below:

Reprint specification with the attached.

Signed and Sealed this

Twenty-third Day of May, 2006

JON W. DUDAS
*Director of the United States Patent and Trademark Office*

ANTIFUNGAL BOTANIC EXTRACTS AND RELATED COMPOUNDS

TECHNICAL FIELD

The invention relates to a new class of general antifungal compounds obtainable from plant species of the pepper, and ginger families, and chemically related species useful in the treatment of fungal disorders.

BACKGROUND ART

There is a wide array of fungi pathogenic to man and animals. The disease they cause are classified into two broad categories; as deep tissue, or systemic mycoses, and superficial mycoses.

Deep tissue, or systemic mycoses including aspergillosis, blastomycosis, coccidioidomycosis, cryptococcosis, histoplasmosis, paracoccidioidomycosis, entomophthoromycosis and candidiasis may involve widespread growth, and dissemination of fungi in internal organs, and tissue. The lungs, brain, bones, spinal fluid, liver, heart, kidneys, other internal organs, and skin being subject to infection that can be life threatening.

Prevalence of deep tissue mycoses is on the rise due to the high susceptibility, and ever growing number of immunocompromised patients. These include cancer, organ transplant patients, and others on immunosuppressant medication, and particularly with patients suffering from immune disorders such as acquired immune deficiency syndrome (AIDS).

Antibiotic drugs such as penicillin, tetracycline, and sulfa ect., though often effective against bacterial infections, are useless against infections caused by fungi. Treatment with a separate group of antifungal, or antimycotic antimicrobial drugs is required.

Antimycotic drugs were first introduced in the 1950's with nystatin (1954), amphotericin B (1958), and griseofulvin (1959). These drugs were originally administered systemically. Tolnaftate was introduced in 1965 as the first effective topical antifungal treatment. Since the 1970's, a number of "azole" derivative antifingals such as clotrimazole, miconazole, econazole, ketoconazole, and others have made their appearance as antimycotics for both systemic, and topical administration. The more current trend has been toward the development of a "triazole" class of antifungals, including fluconazole, terconazole, and itraconazole etc.

Systemic treatment with antimycotic drugs is prolonged, very expensive, and dangerous, with many adverse effects. Complications arising from therapy can itself be life threatening due to the high toxicity of these drugs. The risk of damage to internal organs, adverse effects on blood composition, and adverse reactions to other medications is a very complex matter that must be carefully monitored by administering physicians. With this, other less severe, yet unpleasant side effects, include nausea, vomiting, headache, dizziness, fever, diarrhea, and many others that contribute to complications, and the misery and ill health of the patient. Other adverse effects, now unknown may yet be discovered.

Amphotericin B, given by injection in the treatment of systemic fungal infection, carries with it the risk of liver and kidney damage, and can also result in blood disorders. It interacts negatively with many cardiac medications, and diuretics, as well as other antibiotics.

Griseofulvin, usually taken orally, for fungal infections of the skin, hair, and nails, has a risk of liver damage. Reduced bone marrow function, with lowered white cell levels is another possible adverse effect of treatment. Drug interactions with anticoagulants, and barbiturates reduce effectiveness, and the risk to pregnancy often forbids treatment.

Ketoconazole, taken orally for systemic fungal infections, also carries the risk of liver damage as a result of treatment. The effectiveness of ketoconazole is diminished by interaction with various antacids, and other gastric medications. Ketoconazole increases the potency of other drugs, and is reduced in potency by some antibiotics.

Miconazole, taken by injection for fungal infection of the lungs, brain, kidney, and lymph nodes, can alter blood chemistry resulting in anemia. Miconazole also interacts negatively with medications for diabetes, epilepsy and anticoagulants. The effectiveness of amphotericin B is reduced by miconazole.

Nystatin, taken orally for candida disorders, is of little use in the treatment of systemic fungal infections. Though having far fewer adverse side effects than the other antifungal drugs, it is ineffective against most fungal infections except candida, and aspergillus, making it of limited usage.

These adverse effects are particularly devastating to immunocompromised patients, those in most need of treatment. Complications from treatment may well end their life.

Similar problems of low effectiveness, prolonged treatment, and high cost of prior art antifingals affect the treatment of superficial mycoses.

Superficial mycoses, also called dermatophytoses the skin, hair, nails, or mucosal linings are infected with any of three dozen or so different species of yeast and fungi. More specifically, ringworm (tinea) in it's various forms including athlete's foot (tinea pedis), favus, or scalp ringworm (tinea capitis), body ringworm (tinea corporis) jock itch (tinea cruris) etc., and skin, and mucosal candidiasis among others.

The National Health Survey of 1971–1974 projected from its sampling that about one out of every twelve people in the United States had some form of dermatophytosis, with men being four times more likely than women to contract infections.

Surveys of other nations reveal a much higher incidence of superficial mycotic diseases, among the poor, and underdeveloped countries of Africa, Asia, South America, and those areas of the world having tropical climates.

Though not considered life threatening, as some deep tissues disorders can be, the superficial varieties assuredly take a fair toll in misery, inconvenience, and expense.

Certainly anyone with painful cuts on the feet, bald patches on the scalp, unsightly thickening, brittleness, and discoloration of the fingernails, or an unsightly, itchy rash due to a chronic fungal infection may feel they have a serious illness.

Certainly, the economically disadvantaged would consider any disorder that in addition to causing discomfort, could cost them several hundred dollars a year in treatments without cure "serious".

Likewise, those in the livestock industry may think of ringworm as a serious disease when herds are refused because of ringworm infestation. Being highly contagious, this can occur in just a few weeks without remedy.

Prior art treatments for superficial mycoses, in addition to being expensive, require repeated application before improvement can be seen in the patient. Currently available over the counter treatments, containing clotrimazole, miconazole, tolnaftate, or undecylenic acid, recommend up to sixty applications of the product in order to provide full benefit. More treatments are often required.

Even prescription topical antifungals, administered by a dermatologist, may require as many as two hundred applications over a period of three months to cure some cases of athlete's foot alone. Nail infections may require eighteen months of multiple, daily treatment to provide cure. In addition to being very expensive and time consuming, applying the medicine repeatedly each day is bothersome. Coupled with the discomfort of the fungal disorder, the expense, and inconvenience associated with the treatment adds further to the misery of the condition.

Regardless of economic impact, even wealthy individuals, with the best health care available suffer with all the others when it comes to the discomfort, and bother of repeated application of medication that is slow acting, and often ineffective at producing cure or relief of symptoms.

The current cost of treating ringworm and other superficial mycoses excludes the economically disadvantaged, who suffer most from the condition, from receiving treatment. Poor sanitation and a lower standard of general health adds to the greater prevalence of ringworm, and other superficial mycoses among the poor, and because it is rarely treated because the effectiveness of treatment does not justify the expense.

In this respect, the current array of prior art antifungal treatments have failed. In addition to the misfortune of not having viable treatment for tens of millions of sufferers of fungal infection, no markets are created, and no products sold, to the advantage of no one. Prior art antifungal treatments keep the price of treatment high, the market volume small, and undiverse, and only bring marginal relief to a relative few of the many suffers.

Cost, and ineffectiveness prohibit use of prior art topical antifungals in the livestock industry, as well. The cost of the medicine, coupled with the labor required for repeated application to livestock, forbids the creation of a significant market for these medicines within the industry.

Livestock infected with ringworm are refused by feed lots. Being highly contagious, ringworm can spread through a herd within a few short weeks, not allowing enough time for treatment and recovery in the weeks prior to going to market, even if the animals are treated.

With the current way of topical antifungals, treating food animals for ringworm is an absurd notion. The cost of applying a medicine, perhaps fifty times, to a single head of livestock could never be justified. For this reason, treatment is withheld, to the disadvantage of both the rancher and the animal, which in addition to suffering discomfort, spreads the disease to other animals, perpetuating the cycle further. In addition to money lost, no viable solution is offered by pharmaceutical manufacturers which would otherwise enjoy a new very large potential market.

Whether or not one feels the economic impact of superficial mycoses, all suffers experience the inconvenience of having to make repeated application of currently available prior art topicals. The necessity of making repeated applications is an indication of weak drug action, the great flaw of prior art antifungal treatments.

Topical treatment of superficial mycoses is much safer than internal treatments. The weak action of prior art topical antifungal medications often necessitates the use of systemic treatments, which are more dangerous, costly, time consuming, and associated with many other unpleasant adverse effects mentioned above.

The focus of the prior art upon the development of azole derivatives will continue to keep the cost high, and the effectiveness of antifungal treatments low to the detriment of patient and healthcare economics. The newer generation triazole derivatives, including fluconazole, terconazole, itraconazole, and others, cost many millions of dollars to develop, and apparently are not that much more effective than the prior generation imidazole derivatives, and certainly are doing nothing to make treatment more affordable, or convenient. Beside this, they have much narrower application than the imidazoles, and are considered auxiliary, and not mainline treatments.

It seems doubtful that the azole groups will produce derivatives of significantly greater effectiveness in the treatment of fungal disorders, than what is currently available with prior art treatments. The need for a safe, effective, and low cost treatments is more urgent than ever.

The high cost, low ineffectiveness, and dangerously high toxicity of prior art medications is not suited to deal with the steadily rising number of cancer, AIDS, and immunosuppressant drug treatment cases reported now, and anticipated for the future.

The importance of having medications that are cost effective as well, is becoming critical to the preservation of our very way of life. Escalating health care costs are the primary contributor to the national debt. The high cost of health care insurance in the United States now exclude 1 in 6 Americans from coverage while consuming a greater share of the household budget with each new year. Money otherwise spent on housing, college, retirement, entertainment, and consumer goods must instead go to cover the cost of health care. In addition to a lower standard of living, this takes capital away from industries that provide employment, and tax revenues that pay the national debt.

Should economic ruin be a necessity of adequate health care? Is trading bodily ills for economic ills the only viable option?

People of developing countries of the world experience near total exclusion of healthcare because of cost.

DISCLOSURE OF INVENTION

Several objects and advantages of my invention include an improved treatment for fungal infections of unparalleled effectiveness. A treatment that saves the lives, and misery of millions of sufferers. A low toxicity treatment for fungal infections. A low cost treatment for fungal infections also affordable to the poor. A treatment for fungal infections of broader commercial feasibility. A treatment that saves billions of dollars annually. A treatment that becomes a model for demonstrated savings in healthcare costs including government sponsored healthcare programs such as Medicare, and Medicaid. A veterinary treatment for fungal infections.

I have discovered that pepper, and chemically related compounds, and species of plants contain active agents of unparalleled effectiveness in the treatment of superficial fungal infections. These agents may be administered in the wide range of commonly used drug vehicles and carriers in the form of a lotion, drops, tincture, plaster, aerosol, and other vehicles with a level of effectiveness truly generations ahead of currently available prior art antifungal.

Ringworm in its various forms, including athlete's foot, jock itch, and favus, along with other types of dermatomycoses such as candida, may be completely healed in as few as a single treatment with this medication. Body and scalp ringworm lesions disappear, usually within the first day after treatment, and require no follow up dosage. Recalcitrant cases of athlete's foot are healed in as few as half a dozen doses of my medicine rather than scores of applications, usually required by prior art antifungal medications that often do not cure.

Currently available prior art over the counter topical treatments for ringworm containing clotrimazole, miconazole, tolnaftate, or undecylenic acid, usually require several weeks of daily multiple treatments before improvement can be observed in the condition. In addition to the considerable expense of having to buy several containers of the medication, the time, and inconvenience involved in making repeated applications with meager results adds further to the misery and discomfort of the disease. Even mild to moderate cases of tinea can easily require more than sixty applications of these products before the condition improves. The weak therapeutic action of these prior art, over the counter treatments is often insufficient to produce adequate results. Often, the disorder must be treated by a physician, using prescription topical, and systemic antifungals taken internally.

Prescription treatment with antifungal medications is the most expensive of all treatments. Beside the cost of having an attending dermatologist, the medications themselves are more expensive than the over the counter varieties. This type of treatment, being the best the prior art has to offer, still may require several months of multiple daily doses of the antifungal medication to cure some kinds of ringworm. Treatment for athlete's foot may require up to three months of multiple daily doses of the medicine before the condition can be cured. Ringworm infections of the toe nail can take up to eighteen months to heal. So adding the expense of visits to a dermatologist, time lost from work or leisure, the time and inconvenience of applying the medicine, the cost of the medicine, and the ongoing discomfort of the disorder, all have an economic impact that is quite considerable, in addition to the discomfort of both the disease and the side effects of treatment.

With my treatment, systemic treatment of superficial disorders is likely a thing of the past.

The high effectiveness of pepper appears to be due to multiple therapeutic actions in addition to direct antifungal action. Case observations suggest general healing, keratolytic, immunostimulation and modulation, adjuvant, drug delivery, and prophylactic properties beyond direct fungicidal. In vitro antifungal screens prove proportionally increased potency against terminal drug resistant fungi strains.

It appears that the high nutrient concentration found in pepper including vitamins, minerals, carotenoids, lipids, and others assist the above therapeutic effects addition to the pungent compounds. Pepper compounds are safe, and have been in widespread use as food for thousands of years and do not induce illness as do prior art antifungals.

As a generally recognized as safe (GRAS) listed nutrient food compound, pepper medications are ideal for livestock use. Systemic treatments, and topical medications to control ringworm, candida, and other disorders can be developed. Pepper derivatives may be added to feed to prevent systemic disease as well.

The veterinary market for treatment of mycoses can be greatly broadened given the high effectiveness, low toxicity, and very low cost of my medication. Dermatophyte infections such as ringworm need no longer prevent sale of livestock as before.

Prior art topical antifungals have prevented the formation of a market for the treatment of livestock superficial mycoses. To treat food animals such as cattle, with any of the prior art topical antifungals before market is an absurd notion. The cost of medicine, its very slow action, coupled with the very considerable amount of labor required to repeatedly administer the medicine, can not be justified economically. For this reason, no significant market exists within the industry for such products.

With the treatment of the current invention, however, the scope of product possibilities is enlarged by making treatment of these disorders economically feasible.

The many therapeutic properties, and beneficial components found in pepper provide the ideal profile for a systemic treatment for the more serious, and often life threatening deep tissue, and systemic fungal disorders.

Systemic treatment with antifungal drugs, such as amphotericin B, clotrimazole, griseofylvin, ketoconazole, miconazole, nystatin and others, in addition to being expensive and time consuming, have many bad side effects that can further endanger the health of the patient. These drugs, taken internally, carry the risk of damage to liver and other internal organs, and adverse effects upon blood chemistry. Patients receiving such treatments must be monitored for changes in blood and organ function, as a safeguard against serious damage that can result from treatment. Prior art systemic antifungals also interact adversely with a large number of other medications, another area that requires close attention by the attending physician. Beside this, other adverse effects include nausea, vomiting, diarrhea, fever, headache, anemia, and other unpleasant symptoms that accompany the discomfort of the disease.

The high cost, low ineffectiveness, and dangerously high toxicity of prior art medications is not suited to deal with the steadily rising number of cancer, AIDS, and immunosuppressant drug treatment cases reported now, and anticipated for the future.

Pepper compounds are an important research tool in the war against the increased incidence of life threatening deep tissue, and systemic fungal disorders.

The impact of commercial implementation of this topical antifungal treatment alone, is to make affordable to even the poorest people of developing countries a certain cure for even the most severe cases of superficial mycoses who are now excluded from care because of the high cost, and low effectiveness of prior art antifungals.

A treatment that cures completely in much less time, in a much safer way, without the need of an attending physician, and for less than one penny on the dollar for what is required of prior art treatments in will bring relief to many hundreds of millions of sufferers, rich and poor alike while expand the consumer demand base for products accordingly.

Full scale implementation of these medications will save in excess of $20 billion dollars in Gross National Product in the treatment of superficial disorders in the U.S. alone not to mention the world.

This enhanced level of safety, effectiveness, and dramatic cost savings of these medications should serve as a model to government healthcare programs such as Medicaid, and Medicare save billions of dollars in medical expenditures while providing the best care for recipients.

Now and finally, an antifungal treatment exists that can save our nation, and many nations of the world millions of dollars each day in medical costs, and lost productivity, provide highly lucrative products for commercial exploitation, provides an important research tool in the treatment of life threatening illness, and bring speedy relief to hundreds of millions of suffers of fungal disorders, and perhaps even save lives; man and animal alike.

BRIEF DESCRIPTION OF THE DRAWINGS

FIG. 1 is a molecular diagram of phenol.

FIG. 2-13 show molecular diagrams of compounds of the current invention.

Figure 2:
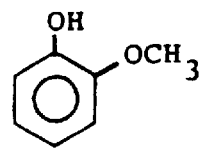
FIGS. 2–13 show molecular diagrams of compounds of the current invention.

FIG. 2 is a molecular diagram of ortho-methoxyphenol.

FIG. 3 is a molecular diagram of vanillyl.

Figure 4:
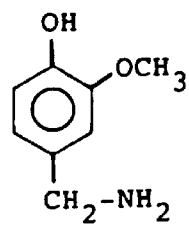

FIG. 4 is a molecular diagram of 3-methoxy-4-hydroxybenzylamine.

FIG. 5 is a molecular diagram of vanillylamide.

Figure 6:
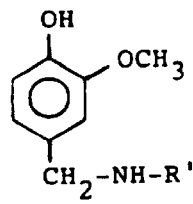

FIG. 6 is a molecular diagram of the capsaicinoids.

FIG. 7 is a molecular diagram of piperidine.

Figure 8:
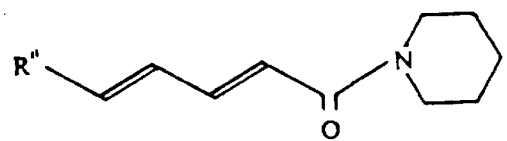
Figure 8:
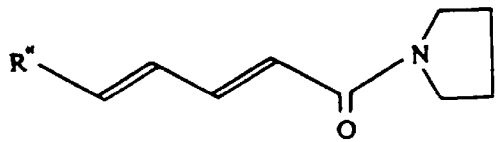
Figure 8:
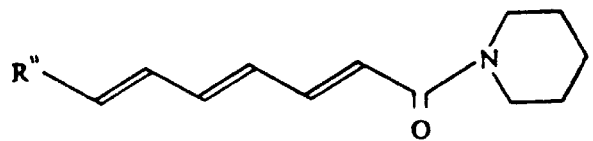
Figure 8:
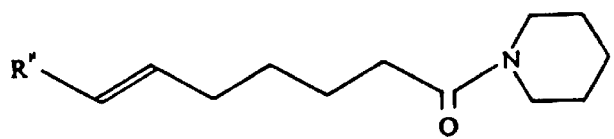
Figure 8:
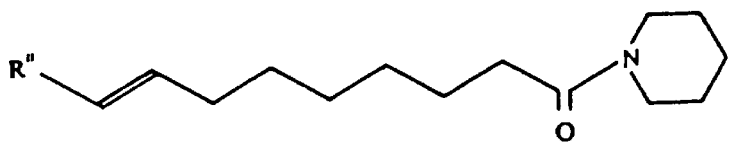
Figure 8:
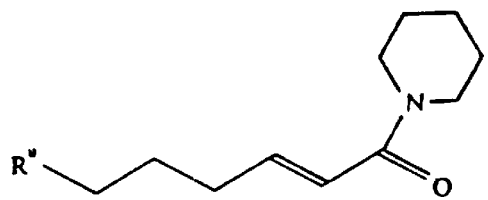
Figure 8:
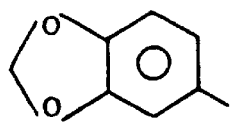

FIG. 8 is a molecular diagram of the pungent alkaloid principals of pepper.

Figure 9:
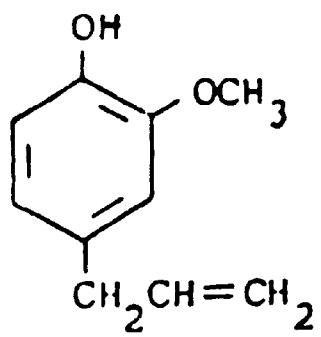

FIG. 9 is a molecular diagram of eugenol.

Figure 10:
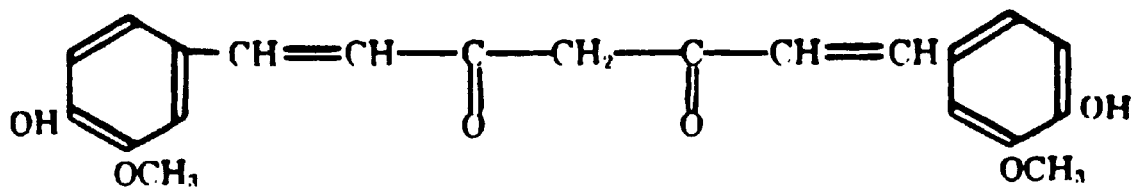

FIG. 10 is a molecular diagram of curcumin.

Figure 11:
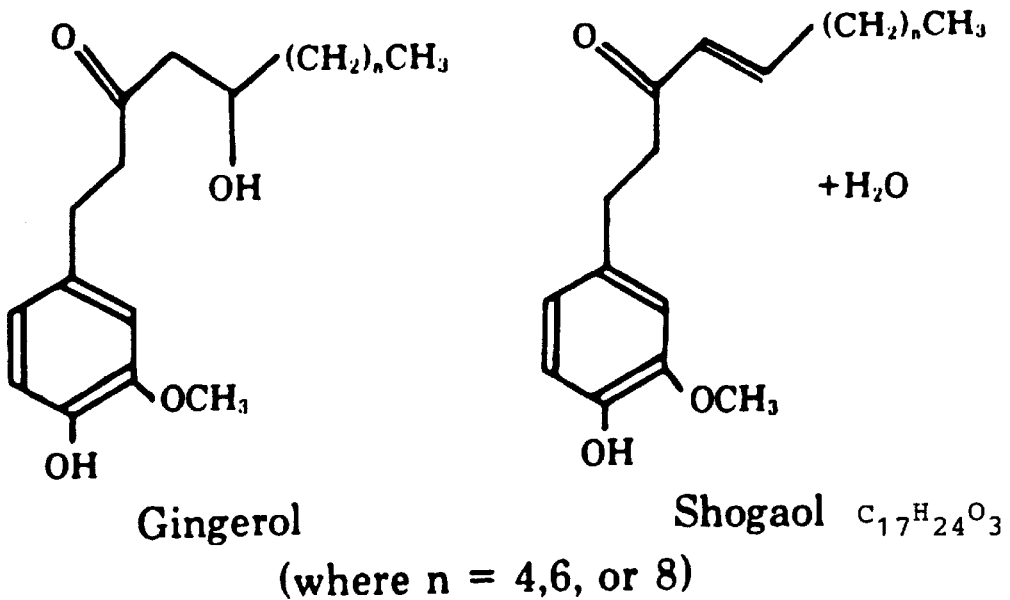
Figure 11:
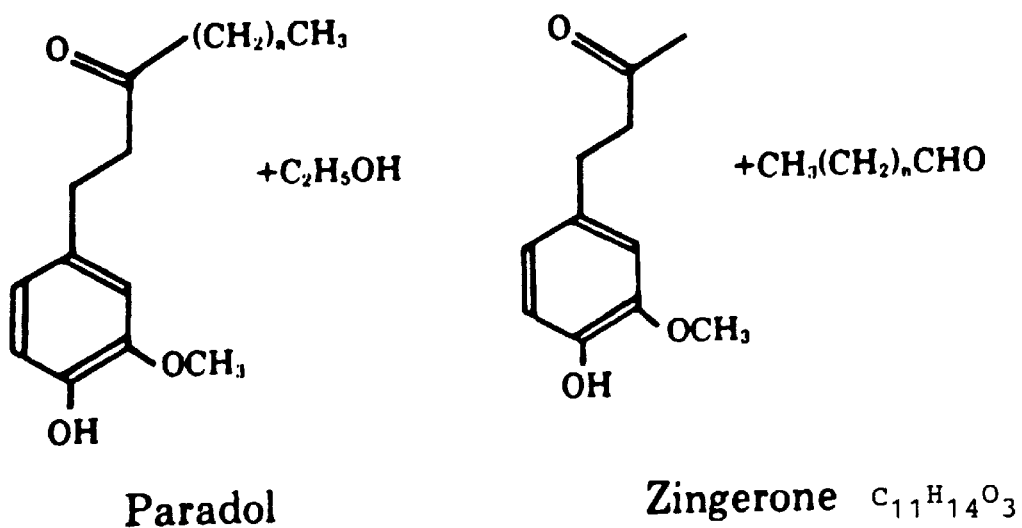

FIG. 11 is a molecular diagram of gingerol.

Figure 12:
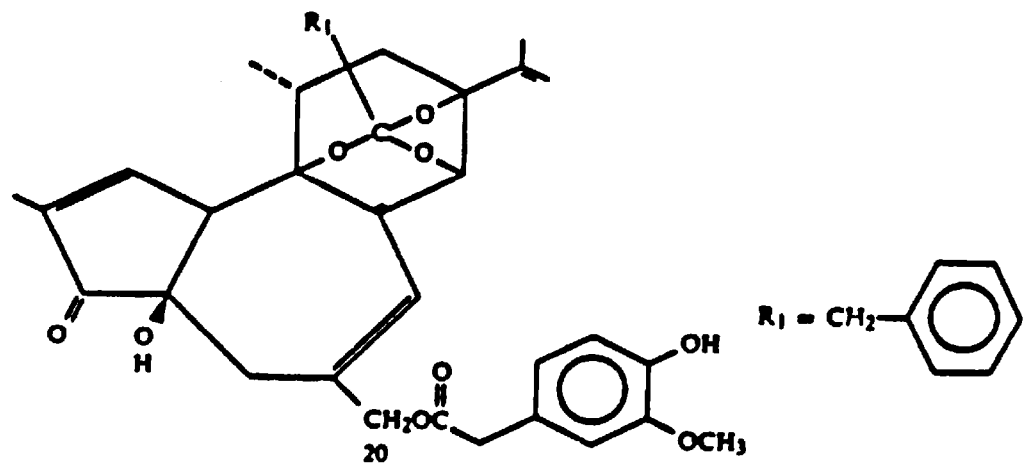

FIG. 12 is a molecular diagram of resiniferatoxin.

Figure 13:
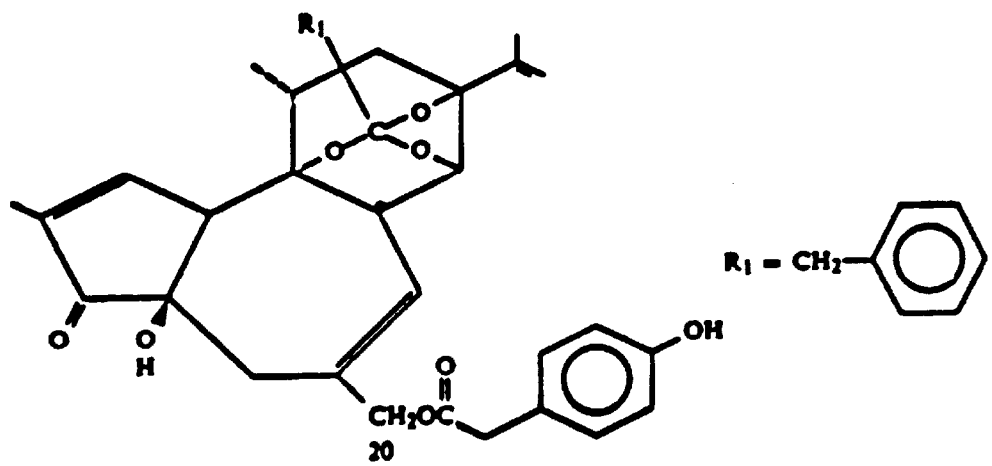

FIG. 13 is a molecular diagram of tinyatoxin.

BEST MODES FOR CARRYING OUT THE INVENTION

A medicinal preparation of pepper, and its active constituents may be administered in a wide range of conventional drug vehicles and carriers. Capsicum, and black pepper are available commercially as oleoresin, in a wide range of concentrations, and pungencies, and may be used in place of the plant product described below.

The preparations described below are made from a moderate pungency commercial grade of ground cayenne pepper (*Capsicum frutescens*), or black pepper (*Piper nigrum*), as an indicator of approximate concentration within each carrier. Their equivalents may be estimated, and prepared from commercially available oleoresin, or from any of the pungent principals, some of which are also available commercially in pure natural, or synthetic form.

The term "pepper", or "pepper compounds" are used somewhat generically to be inclusive of related botanicals of the Zingiberaceae family including ginger (*Zingiber officinale*), turmeric (*Curcuma longa*), cardamon (*Elettaria cardamomum*), Melegueta pepper (*Aframonum melegueta*), members of the Euphorbia genus including *Euphorbia resinifera*, poinsettia (*Euphorbia pulcherrima*), clove (*Eugenia aromatica*), allspice (*Pimenta officinalis*) and others such as vanilla having similar constituents may be prepared in the same way as pepper by following the general procedures outlined below in the capsicum pepper illustration below. Included among this list of botanicals is of course the other members of the Solanaceae pepper family including members of the Capsicum genus with the *annuum*, *baccatum*, and *longum* species.

Among the Piperaceae family, species of the Peperoma, and Piper genus which include the *retrofractum*, *nigrum*, and *longum* species. Other species of plants having similar chemistry may also be used in place of the above.

Variations in performance of each preparation will vary with type, and concentration of extract, carrier, and solvent used in relation to pathogenic organism involved. The scientific literature may be consulted for more detailed investigations as to chemical properties, solubility, separation, and quantitation of constituent compounds.

For purposes of research, or the treatment of disease, the individual compounds responsible for the pungent quality of red peppers, and other capsicums may be obtained directly from ground red pepper, according to procedures described in the article "Separation and Quantitation of Red Pepper Major Heat Principals by Reverse Phase High-Pressure Liquid Chromatography" by Patrick Hoffman et. al., in the *Journal of Agricultural Food Chemistry* 1983, Vol. 31, pages 1326-1330. Though several related capsaicinoids have been identified in trace amounts, the major capsaicinoids (FIG. 6) include:

Capsaicin. $C_{18}H_{27}NO_3$
N-[(4-hydroxy-3-methoxyphenyl)methyl]8-methy-6-nonenamide).

Dihydrocapsaicin. $C_{18}H_{29}NO_3$
(N-[(4-hydroxy-3-methoxyphenyl)methyl]-8methylnonanamide). Norcapsaicin.

$C_{17}H_{25}NO_3$
(N-[(4-hydroxy-3-methoxyphenyl)methyl]7-methyl-5octenamide).

Nordihydrocapsaicin. $C_{17}H_{27}NO_3$
(N-[(4-hydroxy-3-methoxyphenyl)methyl]-7-methyloctanamide.

Homocapsaicin. $C_{19}H_{29}NO_3$
N-[(4-hydroxy-3-methoxyphenyl)methyl]-9-methyl-7decenamide).

Homodihydrocapsaicin. $C_{19}H_{31}NO_3$
N-[(4-hydroxy-3-methoxyphenyl)methyl]-9methyldecanamide).

N-vanillyl-n-nonamide. $C_{17}H_{27}N_3$
(N-[(4-hydroxy-3-methoxyphenyl)methyl]-n-nonamide).

Nonanoic acid vanillylamide. $C_{17}H_{29}NO_3$

Decanoic acid vanillylamide. $C_{18}H_{31}NO_3$

Other capsaicinoids, not listed here, are identified in research literature as trace elements within capsicum, and may be used in medicinal preparations as well, along with other analogous compounds.

Capsaicinoids are generally classified as acid amide derivatives of Phenol (FIG. 1). The characteristic pungent, irritating sensory effects of these compounds are typical of acid amides, whether derived from phenol, or piperidine (FIG. 7).

Phenol (FIG. 1), though lacking pungent flavor, is highly corrosive, caustic, and toxic, deriving many of its properties from its basic benzene structure. While this gives phenol certain antimicrobial properties, it is generally considered to be unsuitable for therapeutic use in man, and animals, due to it's and irritating effects on tissue.

With the addition of a methoxy group (OCH3) to phenol, methoxyphenol is formed. In the ortho position, we have ortho-methoxyphenol (FIG. 2), also known as guaiacum, an extract obtainable from trees of the Guaiacum genus. The effect of this methoxy group in part is an increase in aromacy, and a decrease in toxicity, and caustic properties otherwise existing in phenol, yet without apparent decrease in antimicrobial properties. The attachment of hydrocarbon groups to the ring structure, to form higher analogues apparently increases the antimicrobial properties of methoxyphenol, and phenol. It is presumed that the meta, or para isomers of methoxyphenol have similar properties to the ortho, in like manner to the similarities between the phenol isomers.

The addition of the methylene group (CH2) in the para position to ortho-methoxyphenol produces vanillyl (FIG. 3). Like phenol, and methoxyphenol, it is presumed that changing the position of the methylene group to form other vanillyl isomers will produce compounds of similar, although not exact properties to that of vanillyl.

The vanillyl structure on which the capsaicinoids are constructed is also typical of the pungent principals found in ginger (Zingiberaceae) species of plants.

Collectively known as gingerol (FIG. 11): shogaol, paradol, zingerone, gingerol and other analogs, have a different side chain than the capsaicinoids, and lacking an ammonia ($NH_n$) group, are neither amines, or amides like the capsaicinoids or piperidine series. Hydrolysis of gingerols yield vanillyl, and a fatty acid side chain, both of which demonstrate like therapeutic properties to the capsaicinoid hydrolytes.

Also members of the ginger or Zingiberaceaer family turmeric (*Curcuma longa* L) contains the compound curcumin (FIG. 10), actually a vanillal derivative differing from vanillyl by one hydrogen (H) atom having an (CH) substituent, rather than a methylene (CH2) in the para position. This analog differs further with a side chain unique from the others. Cardamon, allspice, clove, black pepper, and many others contain eugenol, another vanillyl analog with yet another hydrocarbon side chain.

Other botanical sources of vanillyl analogs include gum euphorbium, and extract of certain species of the Euphorbia genus, which contain the capsaicin analog resiniferatoxin (FIG. 12), along with its analog tinyatoxin (FIG. 13) and others.

Replacement of one of the hydrogen (H) atoms of ammonia (NH3), with vanillyl, and the replacement of the other hydrogen (H) atom with an organic hydrocarbon group produces vanillylamide (FIG. 5). In the case of the capsaicinoids (FIG. 6), or capsaicin analogs for example, this organic hydrocarbon group is a chain acid (R'), varying from about 8, to 14 carbon atoms, depending upon the particular capsaicinoid. These side chains, both saturated, and unsaturated (including add to the pungency of capsicums, and themselves possess antimicrobial properties of their own, without apparently contributing corrosiveness, or toxicity to vanillylamide.

Hydrolysis of capsaicinoids yield active agents as well. The splitting off of the side acid chain, and it's replacement with a hydrogen (H) atom yields the primary amine vanillylamine, or 3-methoxy-4-hydroxybenzylamine (FIG. 4) from vanillylamide (FIG. 5), in the case of all capsaicinoids. Conversely, the side acid chain, receiving a hydroxy (OH) group, is converted to a fatty acid, and yields a different hydrolyte for each individual capsaicinoid. In the case of capsaicin (FIG. 6), hydrolysis of the side acid chain R' (FIG. 6) $CO-(CH_2)_4-CH=CH-(CH_3)_2$ yields isodecylenic acid $COOH-(CH_2)_4-CH=CH-CH-(CH_3)_2$.

The piperidine series (FIG. 7 & 8)), represent a group of analogous alkaloid compounds from which most of the pungent principals found within plants of the Piperaceae family, of which black pepper (*Piper nigrum*) is a member, are found. Also classified as acid amides, the piperidine series, like the capsaicinoids found in capsicum species, are primarily responsible for the characteristic sharp, pungent taste of black pepper.

The piperidine ring (FIG. 7) structure is diverse from that of phenol (FIG. 1). Though also a six membered, carbocyclic compound, the piperidine series instead contain one nitrogen (N) hetero atom within the ring. Piperidine is heteroparaffinic, and contains no double bonds. The hetero nitrogen atom within the ring is a contributor to the pungency of these compounds. The attachment of a hydrogen (H) atom to the hetero nitrogen atom within the ring forms the amine structure. Attachment of a hydrocarbon group, in the form of a side acid chain (R" FIG. 8) attached to a benzene structure establishes the acid amide structure. These compounds include; piperine $C_{17}H_{19}NO_3$ (FIG. 8), chavicine $C_{17}H_{19}NO_3$, piperettine $C19_{21}O3N$, piperidine $(CH_2)_5H$, piperyline, piperolein A, piperolein B, piperanine, and others.

Hydrolysis of the piperidine series, like the capsaicinoids, yield active, pungent compounds. Chavicine, for example is hydrolysed to piperidine, which receives an additional hydrogen (H) atom to form a primary amine, and chavicic acid, which receives the hydroxy (OH) group to form the fatty acid.

Hydrolysis of these capsaicinoid, and piperidine acid amides, as well as the other listed compounds may be accomplished with chemical catalysts, or by boiling a liquid preparation in water. Hydrolysis does not appear to diminish pungency, and in some applications appears to enhance both pungency, and therapeutic action.

The carbonyl group (C=O) side chain substituent, common to all the above compounds (except eugenol) is also believed to be a contributor to antifungal activity.

Other active agents found within capsicum include citric acid, vitamins A, B1, B2, C, and E, iron, potassium and niacin in significant quantities, along with other lipids, and carotenoids including capsanthin, capsorubin, and others. Vitamin C concentrations of 100 milligrams per ounce, are the highest of any natural food compound. Vitamin A content is also high, with 6170 I.U. per ounce.

An infusion of pepper may be prepared by soaking approximately 4 cm3 (¼ teaspoon) of commercially available ground red, or black pepper, to one liter (1 quart) of water of sensibly comfortable temperature. Set at least ten minutes before use for best results. Strain plant residue before use if desired.

A more potent tea uses about 16 cm3 (1 teaspoon) of ground pepper for each liter(quart) of sensibly comfortable water. Tea may also be prepared from boiling water, or itself be boiled in water before use. Boiling pepper in water assures complete hydrolysis of the pungent principals, which are also active agents.

A tincture may be prepared by soaking ground red, or black pepper in a solution containing approximately 60% ethanol, and 40% water. Pure ethanol, and other solvents such as acetone, chloroform, vinegar (acetic acid), and others may also be used. The fluid volume of the solution may be about three, or four times that of the dry volume of the ground pepper. The mixture should be agitated, at least occasionally, over a period of at least two hours, with maximum extraction being obtained after about six hours. Allowing the mixture to sit over night produces excellent results. Strain off the residual ground pepper.

A preparation of pepper drops may be obtained by reducing tincture through heat, or passive evaporation. Drops made by this method are similar in purity to some grades of commercially available oleoresin.

A plaster, or poultice may be prepared by mixing ground pepper with water, until it has a paste-like consistency that will assure good adherence to the skin, or cloth to which it is applied.

A lotion, cream, or shampoo may be obtained by adding to any commercially available shampoo, cream, or lotion, a portion of drops, or tincture equal to approximately 25% of the volume of lotion, cream, or shampoo carrier.

A douche is prepared from infusion, or tea that is strained of the plant residue material before use.

A suppository is made from drops in cocoa butter, or gelatin in the same strength as douche, or lotion.

An injection is prepared from a purified version of infusion, tea, drops, etc., administered intravenously, in tissue, or mixed with, and injected into the spinal fluid.

A powder is pepper in ground form, or extracts mixed, and/or bound within a binding powder carrier such as talc.

A pepper impregnated fabric include clothing, and shoe liners made from capsicum wool, or any other pepper compound as a safeguard against harboring these pathogens within one's clothing. For individuals who, for example, have a natural proclivity for contracting athlete's foot, socks, or shoes with liners impregnated with pepper may be worn to prevent contamination leading to infection. The same applies to undergarments, and athletic wear, or anything that has contact with the skin, and is a potential contagion of infection.

Treatment recommendations given below are general guidelines and may be altered to suit specific conditions. If one recommended concentration appears unsuitable, the next graduation should be used.

Consideration as to the degree of tissue damage, patient sensitivity to the medication, and certainly how anxious the patient is to be rid of the disorder. In most, if not all dermatophyte infections, should see results not within the first few weeks of daily treatment.

In the lower concentrations, an infusion may be used in the treatment of milder microbial infections including dermatophyte infections, particularly when tissue damage is minimal.

Infusion works well as a scalp rinse, a bath for the feet, and skin, and as a douche in the treatment of candida, and other vaginal disorders. Infusion is also recommended if patient sensitivity to the higher concentrations becomes significant.

In higher concentrations, a tincture, a powder, a poultice, and a preparation of drops are recommended in the treatment of severe dermatophytosis. High concentrates, such as these, are preferred where tissue damage is significant, and where infection sites are causing considerable discomfort for the patient. Drops for example, work well for topical treatment of nail infections, ringworm lesions, and infected hair. These high concentrates generally produce cure after the first dose when treating skin lesions, and have a prophylactic action of greatest duration, lasting up to about five days after application. As it is usually necessary to induce substantial healing of the skin as a measure against recontamination, and reinfection of dermatophytes, the higher concentrates appear to be most effective as prophylactics.

A tea represents a moderate concentration of pepper compounds. It may be used in the same manner as infusion, or in the treatment of more severe cases of dermatophytosis. Tea should be used if infusion fails to bring immediate relief of secondary symptoms, such as itching in athlete's foot, candida, or jock itch, within one hour of the first treatment.

Tea may also be used in place of the higher concentration carriers, such as drops or tincture. It is often equally effective in curing severe cases of dermatophytosis, in which there is significant tissue damage, as the high concentrates. In this case, tea is preferred over the high concentrates, particularly if the patient sensitivity to the medication is causing significant discomfort.

Tea is also suitable as a gargle, or mouth rinse for thrush, or other fungal infections of the throat, and oral cavity.

For an injection of pepper compounds in deep tissue, spinal fluid, or intravenously, milder concentrations, such as infusion are recommended for initial treatment. While injection of pepper extracts such as capsaicin have been administered safely in animal testing of analgesics, it is not known at this writing if treating humans by injection has been attempted.

A lotion, or shampoo may be prepared with any commonly available lotion, or shampoo, and applied to infected areas in its intended manner. Other therapeutic agents, in addition to pepper extracts, may be added to shampoo and lotion. If irritation is a concern, a topical anesthetic, such as lidocaine, or benzocaine may be added to lotion to reduce severity. If skin is very dry, emollients may also be added to lotion.

A pepper aerosol may be inhaled in the treatment of throat, and respiratory infections. In this administration, aerosol should be derived from a lower concentration such as infusion, as pepper is extremely irritating to the nose, throat, lungs, and eyes, especially when airborne. This is especially true of capsicum aerosol. For this reason, aerosol is somewhat limited in it's medicinal application.

The irritating effects of pepper aerosol, and particularly capsicum, is greater when distributed within an etheric tincture solution, such as alcohol, ether, chloroform, or acetone. Once airborne, even minute concentrations have a tear gas, or mace like effect on the eyes, and respiratory system.

Pepper powder is also very irritating when airborne, and like aerosol, has a more limited medical application than the other carriers. If used as a foot powder for example, it is best to fix the pepper compounds within a powder binder such as talc, to prevent, or lessen escape of airborn particulate.

Below are theories as to the therapeutic actions of pepper compounds based largely on observation, and set forth to further explain the operation of the current invention, and to give direction to areas warranting further research.

The irritating nature of the pungent compounds are instrumental in precipitating a rapid inflammatory response in the area of administration. In sufficient concentrations, this is observed when applied to skin in the treatment of tinea. The area of treatment often turns red, or pink, and feels warm or hot. Burning, or warm tingling is sometimes reported by patients after topical administration of pepper extracts, usually the result of too high a dosage. Though this burning sensation can become quite intense, it does not usually last beyond the first five or ten minutes after treatment. The burning subsides into a warm, tingling sensation that is no longer uncomfortable to patients. The induction of inflammation to the point of pain is accidental, and not necessary for cure. Inflammatory responses associated with even slight warmth and redness are likely adequate to provide sufficient therapeutic action.

Pepper also appears to act as an immunostimulant, by precipitating leukocytes, and other mononuclear cells, along with a variety of antifungal compounds from the blood, and surrounding tissue, to the area of infection. Though done primarily through inducing inflammation, pain and discomfort are not required in order to receive the full therapeutic benefit. Pepper compounds are also believed to aid in the delivery of these antifungal immune responses of the body, and increase their potency in addition to its own antifungal actions.

The therapeutic value of inflammation, is the stimulation of the body's own immune response in the area of infection. This precipitates a varied array of fungistatic serums, including leukocytes, and other mononuclear cells in the area of infection. These fungistatic serums inhibit the growth of pathogenic fungi.

Inflammation also increases the rate of skin shedding, which combats penetration of the fungus, or other organism into the skin. In this mode of action, the microbe is essentially "cast off" with the diseased tissue. Perhaps or this reason, those varieties of dermatophytosis that are accompanied by inflammation often eventually heal on their own. The noninflammatory varieties such as dry athlete's foot, however become chronic, and are very difficult to heal. The lack of participation of the immune responses of the host prevents healing, and cure.

It is further possible that pepper compounds act as an adjuvant to these fungistatic serums, by facilitating delivery through blood vessel, skin, and fungal cell membrane pathways. Being composed primarily of lipids, capsicum, for example, may increase the permeability of the cellular membrane of both host, and fungi. In addition to aiding delivery of antifungal serum, the increase in cell membrane permeability may facilitate the delivery of undecylenic acid, another antifungal compound found in sweat, into the fungi. With the aid of increased permeability provided by pepper compounds, antifungal compounds which are normally fungistatic, become fungicidal.

Apart from host response possibilities, the direct antimicrobial properties of pepper and another of the notably pungent botanicals ginger are observed in vitro, in addition to those observed in the actual treatment of disease.

A series of in vitro tests are conducted on 3 tincture samples prepared from the ground spice of cayenne pepper (Sample A), black pepper (Sample B), and ginger (Sample C). Each spice is measured, and mixed with pure ethanol in an amount three times the measured volume.

The mixtures are stored for 18 hours at room temperature (22° C.), and agitated on 5 separate occasions over the period. The mixtures are then strained of residue, and submitted for testing. Also included is Sample F; a tincture prepared with commercially pure capsaicin (8-methyl-N-vanillyl-6-nonenamide) at a concentration of 25 mg./ml. pure ethanol.

Initial in vitro tests performed by a medical university laboratory report that none of the Samples A, B, C, or F show antimicrobial activity against Candida albicans, or Neurospora crassia on a solid medium, carrot juice agar (pH 6) screening.

A liquid assay in vitro screen performed by a major U.S. pharmaceutical company however, reveals activity against all 11 strains of pathogenic fungi tested, including 7 strains of Candida. These pathogenic strains are responsible for deep tissue mycotic infection, although the Candida strains also cause superficial mycotic infections of the skin, and mucosa as well.

At first glance, a general hierarchy of activity relative to the degree of pungency among the botanical Samples A, B, & C is evident, with cayenne pepper being most pungent, followed by black pepper, and then ginger. Though exceptions are evident in the tests, degree of pungency is an accurate general "rule of thumb" with regard to evaluating the relative effectiveness. This observation however, for reasons set forth below, should not be interpreted as an indication that therapeutic affects are determined solely by the degree, and quantity of pungent principals present, though it is a factor. This will be further addressed below.

Perhaps most intriguing of the test results below is that Samples A, B. C, & F of the current invention show greatest activity against those fungal strains most resistant to the drug standard Amphotericin B. In particular, C. albicans ATCC 38247, C. kefyr ATCC 28838, and T. glabrata ATCC 15545 show particular sensitivity to Samples A, B. C, & F in this screen. These strains, being most resistant to standard drug therapies, pose the greatest potential for causing life threatening illnesses. The necessity of prolonged treatment with high dosages of highly toxic antifungal drugs required to treat these diseases is often itself life threatening to the patient.

Another important feature of these test findings is evidence of the presence of multiple antimicrobial compounds within the Samples. In comparing Samples A & F for example, it is apparent that the antimicrobial action of cayenne pepper (Sample A) cannot be wholly attributed to the presence of capsaicin alone in the ground spice.

A review of the aforementioned article "Separation and Quantitation of Red Pepper Major Heat Principals by Reverse Phase High Pressure Liquid Chromatograph" indicates by rigorous testing a total "capsaicinoid" content not exceeding about 1.9 mg./gram in common red pepper. Sample A being diluted 3 times with ethanol would fix its maximum capsaicinoid content at perhaps 0.063%, or about 630 μg./ml. Capsaicin accounting for about half of the total capsaicinoid content of common red pepper, would fix the capsaicin content of Sample A at about 0.032%, or about 320 μg/ml. This diluted 256 times shows Sample A as having activity against C. albicans ATCC 38247 at a capsaicin concentration of less than 1.25 μg./ml., and total capsaicinoid content of less than 2.5 μg./ml against which Amphotericin B requires a concentration of 25 μg/ml. Additionally, capsaicin though the most toxic compound found in any significant amount in capsicum peppers, is much less toxic than Amphotericin B.

In comparison, Sample F has a concentration of pure capsaicin at 25 mg./ml.—about 40 times the total capsaicinoid content of Sample A, yet is still short of the Sample A performance across the board. This can only mean the presence of another antifungal compound, and/or a synergistic relationship between the mix of capsaicinoids and other compounds within the botanical that account for the total antimicrobial effect. It may also suggest that the therapeutic actions of these botanicals are not generally improved by extensive isolation of their individual constituents, and that the total therapeutic mechanism involved is quite complex, involving a substantial number of compounds in addition to the phenols, and piperidine compounds present. In this respect, isolation of individual constituents produce the undesirable effect of to some degree dismantling the full therapeutic action of the compound.

Sample F is the exception containing a purified isolate (capsaicin) of the primary pungent principal found in red pepper and other capsicums. Sample F also has perhaps 3 times the capsaicinoid, and 6 times the capsaicin content of the most pungent species of capsicum known to exist in nature. Yet across the board, Sample F falls short of the basic botanical extract Sample A even though it has 40 times the capsaicinoid concentration of Sample A.

While the above tests provide important insight into some of the therapeutic actions of the current invention, they are of course only partially indicative of the fill antimicrobial action present, even as the earlier carrot juice agar tests failed to reveal any activity at all. The filler antimicrobial activity of the compounds described above are of course observed in the actual treatment of disease, wherein the bodily immune responses are also perhaps modulated. These compounds repeatedly cure dermatophyte infections in as few as a single application. This cannot be said of Amphotericin B, or any of the other currently available prior art topical treatments.

The irritant acid amides found within both kinds of pepper, and their hydrolytes, appear to have direct fungicidal actions. Isodecylenic acid, one of the hydrolytes of capsaicin, may have antifungal properties superior to it's fatty acid chain relative, undecylenic acid, and offer important clues to the development of still other antimicrobials, structured similarly for increased effectiveness. Another hydrolyte of the capsaicinoids, 3-methoxy-4-hydroxybenzylamine (FIG. 4), suggests a new class of amine antimicrobial compounds, derived from this, and other analogous structures.

| Organism | Minimum Inhibitory Concentration | | | | |
|---|---|---|---|---|---|
| | test sample (number of dilutions) | | | | standard |
| Amphoter.B | A | B | C | F | ug/ml |
| Candida Albicans ATCC 10231 | 16 | 16 | 8 | 8 | 1.56 |
| Candida Albicans 579a | 16 | 16 | 8 | 8 | 1.56 |
| Candida Albicans 442 | 16 | 16 | 16 | 16 | 1.56 |
| Candida Albicans ATCC 38247 | 256 | 16 | 8 | 256 | 25.00 |
| Candida Albicans ATCC 62376 | 16 | 16 | 8 | 8 | 1.56 |
| Candida tropicalis NRRL-Y-112 | 16 | 32 | 16 | 16 | 1.56 |
| Candida kefyr ATCC 28838 | 64 | 32 | 16 | 16 | 3.12 |
| Torulopsis glabrata ATCC 15545 | 16 | 32 | 16 | 8 | 3.12 |
| Cryptococcus albidus ATCC 34140 | 4 | 8 | 8 | 16 | 1.56 |
| Saccharomyces cerevisiae GSI-36 | 16 | 16 | 8 | 16 | 1.56 |
| Aspergillus niger ATCC 16404 | 16 | 4 | 4 | 4 | 1.56 |

Spec: Yeast extract Nitrate Broth + Glucose, water solvent, 48 hour Incubation, all Samples precipitate at 50% in YNB + G.
Sample A = cayenne pepper*
Sample B = black pepper*
Sample C = ginger*
Sample F = capsaicin (commercially pure 8-methyl-N-vanillyl-6-nonenamide) 25 mg/ml pure ethanol.
*tincture 3:1 ground spice in ethanol 18 hours @ 22C_.

Other possible antimicrobial agents found in pepper plants, that may play a role in producing curative results, are the phytoalexins such as the compound capsidiol, found in plants of the Solanaceae family which includes capsicums. A group of antimicrobial agents not normally present in the plant, phytoalexins are produced by the plant, only in response to trama caused by heat, cold, mechanical injury, or attack by insects, or microbes. Capsidiol, and other of the phytoalexins produced by Solanaceae species, have antifungal properties against fungi that are pathogenic to the plant. While these fungi are not pathogenic to man, it is possible that capsidiol, or another phytoalexin produced in response to their challenge has antifungal action against fungi that are pathogenic to man, as well as those pathogenic to plants. It is therefore possible that capsidiol, or another phytoalexin may play a role in curing fungal disorders in man and animals, as well as plants.

Dehydration is another possible therapeutic action of pepper compounds. In the treatment of superficial mycoses, pepper extracts appear to dry the skin to a degree that may be inhospitable to fungi. Perhaps the result of increased permeability, or the formation of salts on the skin, the skin, though drier, is not uncomfortably so, and may have at least a fungistatic effect.

The prophylactic action of pepper extracts is another important therapeutic possibility. In addition to having apparent immediate fungicidal action in the treatment of superficial mycoses, pepper compounds also appear to remain in the skin for perhaps ten days after treatment, to prevent reinfection. Patients often report the reoccurrence of the warm, tingling sensation in treated areas while bathing, sometimes days after treatment. Exposure to water appears to also restimulate its therapeutic action as well. If feet, or skin become moist, and sweaty, the therapeutic action is intensified, at the same pathogenic fungi would normally proliferate. This provides a shield against reinfection due to recontamination, and protects the skin while it heals.

Pepper compounds also appear to function as a vulnerary, aiding, and accelerating the healing and regeneration of tissue. As tissue damage can be severe in certain forms of dermatophytosis, such as favus, nail infections, and athlete's foot, it becomes necessary to heal the damaged tissue before full cure is possible. Pathogenic fungi, finding opportunity in damaged skin for example, will often continue to reinfect those areas unless the skin is healed. This is perhaps one reason prior art medications are so ineffective towards cure. The skin is not allowed to heal quickly enough to safeguard against repeat infection, as healthy, whole skin is the best protection against reinfection. The particularly high vitamin, and other nutrient content of capsicum for example, may have a further healing effect, as pepper compounds appear to stimulate the healing process of the skin, and encourage regeneration, growth, and normalization of function.

The high concentration of antioxidant compounds such as vitamin E, aromatic amines, phenols, and amino phenols found in pepper, particularly capsicum may also facilitate an antifungal effect beyond a generalized aid to healing. These antioxidants may interfere with the action of digestive enzymes secreted by the fungi, that are necessary for ingestion of nutrition; in effect starving the fungi.

Conversely, the very high concentration of vitamin C, a known oxidant, may also interfere with the ability of the fungi to digest, and ingest nutrition, by instead oxidizing it's food compounds before they can be absorbed.

It is also possible that high concentrations of citric acid, or vitamins found in pepper, are directly toxic to the fungi.

The observed keratolytic action may also have an antimicrobial effect, by perhaps interfering with the ability of pathogenic microorganisms such as fungi to digest, or ingest the keratin on which they feed.

Lastly, it will prove further helpful to witness the dramatic healing effect of pepper compounds in actual treatment of disease.

In a study of eight patients, all infected with various forms of dermatophytosis, complete cure is obtained after one topical application of the medication of the current invention in five of the eight cases studied. The other three cases studied are cured within half a dozen treatments or less. None of the patients are taking any kind of medication for ringworm, or for any other disorder, and no special sterilization measures of clothing, furniture or bedding are taken, beyond otherwise good personal hygiene.

In the first portion of the study, a family of three, all afflicted with ringworm, are completely healed after a single topical treatment with a pepper compound.

The infant has developed approximately six ringworm lesions about the back of the scalp, and back, and right side of the neck. The first few lesions were noticed a month before.

The mother of the infant has about six ringworm lesions on the right arm, most on the outside bicep. The appearance of the lesions was first noticed approximately three months before.

The father of the infant has approximately eight ringworm lesions on the left arm, most on the outside bicep. The right arm has four lesions, also on the outside of the bicep. Four other lesions appear on the shoulders, and lower back. The man first noticed lesions of this type approximately eight years earlier.

On all three subjects, the ringworm lesions have the same general appearance. The lesions are ring shaped, with slightly raised outer borders that are sometimes crusty. The lesions are red, with a smooth, and sometimes scaly interior. A clear, sticky fluid sometimes covers the lesion. The average diameter of the ring is about 15 mm (0.6'), with some as large as 20 mm (0.8'). The lesions appear, and remain for, several weeks, sometimes disappearing, leaving lighter colored skin at the site of the prior lesion.

The man is first to be treated with a preparation of capsicum, wherein a plaster is applied to three lesions on the left bicep. A very slight, momentary tingling sensation is reported. The sensation lasts for about the first five minutes after application, and is not uncomfortable. The plaster is left on the skin for about one hour, then rinsed off with water. Afterward, the lesions appear redder than they did prior to application of plaster. After six hours, the lesions appear to be whiter, with the coloration being more similar to the skin tone of the healthy skin, than prior to treatment. At twenty hours, all three lesions appear healed, as it requires very close examination to reveal the site of the prior lesion. The characteristic patch of lighter colored skin that normally accompany lesions that have healed by themselves is not present.

The other dozen or so lesions found on the man are examined, and found to be substantially unchanged from their last examination the day before. Another examination on the third day yields the same results, with no sign of the three lesions that were treated and healed, and little change in the untreated lesions.

The other dozen ringworm lesions on the arms and trunk of the man, are treated with the same capsicum plaster, with identical results. All twelve lesions, regardless of location, are healed with the exact location of the prior lesion being difficult to determine because of the advanced degree of healing of the skin in that area.

One week later, the woman is treated with the same capsicum plaster as the man, with similar results. At three days after treatment, all six lesions are completely healed in similar fashion to those on the man.

One week after the woman is treated, the infant girl is also treated with the capsicum plaster in the same manner as both her parents, and is healed in the same way, with the disappearance of all lesions within about one day. It is also interesting to note that the infant girl displays no sign of discomfort when the medication is applied, and does not cry, or even appear to take notice of the treatment.

Regular examinations of these three patients, over a period of several months, fails to identify the reappearance of one single ringworm lesion in any one of them. Each lesion of the patient is completely healed of ringworm, after just one single topical treatment with my medicine, 100% cure of twenty-eight lesions on three subjects is accomplished after a single dose of my medication, without reappearance of a single lesion. This is done without sterilization measures, and aside from any other medication whatever.

In another portion of the study, a woman in her middle thirties is healed of athlete's foot within hours of a single treatment of my medication. The woman works a full time job, in which she is required to be on her feet most of the time. Approximately one week after having purchased a more comfortable pair of shoes for work, the woman develops an inflammatory variety of athlete's foot. The primary symptoms are intense itching on top of the toes and foot, felt mostly in bed at night, along with a bad, musty foot odor. The itching is now interfering with sleep each night.

The woman soaks her feet in a bath, prepared from infusion of capsicum, for fifteen minutes. The woman reports a warm, tingling sensation that lasts about ten minutes. This treatment is administered at 8:00 p.m. The woman retires for the evening at 10:00, and does not experience any of the itching characteristics of the previous evenings. For three weeks the woman reports not a single recurrence of the itching on the feet She continues to wear the same footwear as before, and does not take any kind of sanitary, or other precautions to avoid reinfection.

After about three weeks, the woman begins to notice a gradual return of the itching on top of the feet that she had experienced before. Within another week or two, the itching is as intense as ever, and is again interfering with sleep.

The woman's feet are treated with a lotion of capsicum, using raw aloe vera gel as the lotion carrier. Lotion is applied to the feet, and rinsed off with water at the end of half an hour. The treatment is administered at 8:00 in the evening, before the woman retires for the evening at 10:00. The woman reports no itching that evening, nor afterwards, for many months. She disposes of the comfortable shoes, she had bought for work, and has no further recurrence of athlete's foot symptoms. The woman is completely healed of athlete's foot after just one single treatment with my medication.

The sixth case involves a five year old girl, who is completely healed of a recalcitrant case of dry athlete's foot. Prior to treatment, the child's feet are peeling severely in the areas between the toes, and on the entire sole of the foot. Loose skin, in pieces as large as about 4 mm (⅛") square are hanging around the lower edge of the ball of the foot. The entire sole of the foot is callused, and has a wrinkled appearance.

Deep cuts occur periodically on the ball of the foot and around the base of the toes, particularly the great and small toes. The child often complains that her feet hurt from the cuts, but otherwise describes no other discomfort or symptoms. The girl has had these symptoms for about three years, since age two years.

At age two years, the girl develops a particular affection for a certain pair of shoes, and wears them constantly, refusing to wear other shoes. Weeks later, the girl develops a very offensive foot odor. Afterward, her feet gradually develop the symptoms described above, becoming chronic over the next three years.

An ethanol tincture of capsicum is applied to the girl's feet. The girl complains about a stinging sensation in the cuts around her great and small toes. The girl cries for about five or ten minutes, then reports that the sting is gone. The girl is also treated with the same capsicum tincture on days three and five, after the initial treatment. The investigator performs these second and third treatments because he is not sure if the first treatment is sufficient to penetrate such thick calluses on the soles of the feet, having never treated such badly damaged skin with this particular treatment.

On day three, just prior to the second treatment, the feet are examined and appear slightly improved. The cuts around the toes have formed scabs, and no discomfort is reported by the girl after application of the tincture.

On day five, the feet are again examined before receiving the third treatment, and again appear to be further improved. The cuts are continuing to scab over and heal, and the girl reports no discomfort from the medicine. This general trend continues for the next several days, yet treatment is not again administered.

By the fourteenth day, the feet are nearly, completely healed. There are no cuts or scabbed cuts, and no pealing or loose skin. The calluses are nearly, completely reduced, and the skin has a healthy color and texture, and no longer has a wrinkled, ragged appearance. It is not possible to determine that the girl has ever had athlete's foot, as her feet are healthy and normal. The child is excited that her feet are "like new again".

On day twenty one, the girl's feet are again examined. The skin around the bottom and sides of the toes has succumbed to reinfection, as the skin is again peeling, though not as severely as before the first treatment.

At six weeks, the girl's feet have returned to the pretreatment condition. The skin on the sole of the feet is thickened and callused. The skin on the soles and between the toes is peeling and has a ragged appearance. Cuts appear periodically at the base of the toes, on the heel and at the ball of the foot. The dry athlete's foot is back in full force.

The reinfection of the girl's feet is not presumed to be the result of recontamination, as no sanitary measures have been taken to prevent reinfection, and the girl continues to wear the same footwear as before the treatment. As these pathogenic fungi find opportunity in damaged skin tissue such as that described, the skin must be healed to prevent reinfection. The best protection from reinfection being healthy, undamaged skin.

This is one reason why the prior art has such difficulty curing this type of ringworm. The therapeutic action of prior art antifungals is so weak and slow acting, it arrests the resident fungi only enough to allow the healing process of the skin a slight advantage.

This is why a case of dry athlete's foot can easily require twelve weeks of daily, multiple treatments with prior art medications to provide cure, which is usually only temporary.

The dramatic improvement of the girl's feet between the last treatment on day five, and the examination on day fourteen suggests accelerated healing over any activity of fungi during this interval. It also suggests a prophylactic action by my medicine that may provide protection for perhaps seven days or more.

Recalling complete cure after a single dose of my medicine in the first five cases leads to the conclusion that the fungi are eradicated on initial contact with my medication. What distinguishes them from this sixth case is the relatively minor degree of skin damage they suffered, in relation to the present case. This further supports the notion of the prophylactic action of my medicine, as seven days or less is ample time to heal the minor skin damage caused by the body ringworm lesions.

In an attempt to determine the maximum duration of capsicum's prophylactic effect, and to compare it's performance with that of synthetic capsaicin, the synthetic version of the primary irritant found within natural capsicum, the girl's feet are again treated.

Prior to treatment, the girl's feet have again returned to their original, recalcitrant condition that was noted prior to the first treatment. The girl's feet are peeling severely on the bottom and sides of the toes, and on the ball of the foot. The skin in this area is thickened, and callused, with deep cracks sometimes resulting in painful cuts. The skin has a wrinkled, dry, and ragged appearance, with intermittent red blotches, occupying about half the total surface area. Small cuts appear periodically around the base of the great and small toes, which often cause pain, especially when walking.

A lotion of capsicum, consisting of 4 cm3 (4 teaspoon) of ground red pepper mixed with 48 cm3 (12 teaspoons) of raw, aloe vera gel, is applied to the child's left foot. The girl describes a tickling sensation as lotion is being applied, and is laughing. About three minutes afterward, the girl begins crying, saying that the cuts on her toes are burning. She continues to cry for about ten more minutes, and afterward indicates that the burning has gone.

At the same time, an ointment of capsaicin, consisting of about 0.03 percent capsaicin (from oleoresin) in turpentine oil is applied to the right foot. There are no cuts on the right foot at this time, and the girl reports no discomfort from the medication.

The medications described above are applied once each week for the next two weeks, and observed regularly over the next three weeks, with little notable change the first few days.

On day three, the feet are examined, and appear to be showing signs of improvement. The peeling does not seem as severe, and the red blotches look as if they are fading. The cuts on the left foot are healing, and show no sensitivity when firmly squeezed with the fingers.

On day four, the feet are again examined, and look much better than the previous day. The peeling is again reduced, and the red blotches have completely disappeared. The right foot looks slightly better than the left, suggesting the therapeutic effectiveness of the capsaicin ointment. The cuts on the left foot show further progress in healing.

Upon examination on the sixth day after treatment, the child's feet look very much improved. The loose skin has for the most part worn away, being replaced by healthy skin that shows no scaling, or discolor. The cuts on the left foot have disappeared, and both feet show reduced skin thickness, and only faint reminder of cracks that are mostly healed. Both feet look about the same, suggesting equivalent therapeutic performance between capsicum and capsaicin preparation.

The examination of day seven reveals little change in the condition of the feet from day six except that they appeared slightly better on day six. Small cuts along the base of the small toe on the right foot are not causing discomfort, as the medicine is applied for the second time.

Subsequent examinations of the next seven days reveal a similar pattern to that of the prior week. Little change is observed the first few days after treatment, with very noticeable improvement being observed between the fourth and sixth day after treatment. This pattern is also established on days eleven through thirteen, yet without substantial advance in the stage of healing beyond that observed on the sixth day.

It is evident that a single weekly application of my medicine produces substantial improvement in recalcitrant cases of athlete's foot. Though this improvement is sustained, it is not usually sufficient to induce fill cure, at least within a three week span.

Nor does the degree of improvement compare to the results of the prior study, in which the medication was applied three times within the first week. Depending upon the case, two to four applications per week should be sufficient to provide complete, and sustained cure for recalcitrant cases of athlete's foot.

To demonstrate a complete cure for recalcitrant athlete's foot, and to compare the performance of a red pepper (*Capsicum frutescens*) extract with that of one made from black pepper (*Piper nigrum*), the girl's feet are again treated. The girl's right foot is treated with an ethanol tincture of capsicum made from ground red pepper, while the left foot is at the same time treated with a similar tincture prepared instead with an equal amount of black pepper.

The girl's feet are treated eleven times, once every other day, over a period of three week's. The pattern of previous tests is also observed in this trial, with both the red, and black pepper tinctures performing with equal effectiveness. As in the other tests with the girl, significant improvement is observed between the fourth, and sixth day after treatment, with dramatic improvement being noted at two weeks. At three weeks, very little sign of the prior disorder remains, and the condition does not return after weeks of observation. The girl is healed of recalcitrant athlete's foot, with just eleven topical treatments over a period of less than three weeks.

In the seventh case study, a woman of sixty is cured of a dry variety of athlete's foot. Prior to treatment, the woman's feet have peeling skin between the toes, and thickened soles with cuts on the underside of the heal.

The woman's feet are soaked in a capsicum tea for fifteen minutes at a time, once a day, for five days. On the second day, the woman complains that her feet are very dry, and that one of the cuts on her heel is making walking difficult because of the pain. By the fourth day, she indicates the cessation of those symptoms. After eight weeks, the feet are examined and the skin appears healthy, with no sign of peeling or thickening of the skin. The woman indicates that after the fourth day of treatment, she did notice the reemergence of symptoms at the time of the eight week examination, and felt cured since.

In the eighth case study, a boy of thirteen is completely healed of a severe fungal infection of the face, and neck after just two weeks of treatment with my medication.

Over a period of nearly five months, the boy has been suffering from what is described as an angry, bright red rash about the face, from beneath the eyes, down to the bottom, and sides of the neck. The boy's father describes the disorder as "literally eating his son's face away". The boy, and his family are for some time quite distressed, as treatment administered by a general practitioner, and two dermatologists over more than four months, fails to heal the condition. The expense of treatment is nearing $1,000 out of pocket. The visits to the physician, have cost the parents more than twenty hours away from work, and the boy must be excused from school the same amount of time. The boy is of course doubly distressed, as in addition to the discomfort of the disease, he must bear the humiliation of wearing this rash on his face that is more horrible in appearance than a severe case of acne.

A skin scraping sent to a laboratory reveals the presence of fungal hyphae, not of the ringworm variety.

The boy is given griseofilvin orally, but must discontinue treatment after one week as a result of severe nausea. The boy is then given tolnaftate topically, and has shown no significant improvement in the condition over a period of several weeks.

The boy is then given lotion prepared with capsicum, and instructed to apply the medication once every other day after bathing until symptoms disappear. All other treatments are also discontinued.

The boy's father administers the treatment as prescribed, and is seeing noticeable improvement by the third day. The condition continues to improve over this period, and by the tenth day the skin is almost completely healed, with barely a remnant of the prior disease remaining. To say the least, the boy's family and friends are amazed, and astounded at the rapidity of cute of this horribly unsightly condition, that had persisted for so many months before without improvement, often referring to the medicine as "a literal Godsend!"

The treatment is discontinued after only two weeks, and the boy is healed without relapse after many weeks of observation even until the time of this writing.

Thus the reader will see from these several examples that treatments containing pepper extracts provide a degree of effectiveness that is many generations ahead of the prior art. Single application cure of dermatophytosis, being unheard of among prior art treatments, is the usual result with the medication of my invention. No longer is it necessary for suffers to endure prescription therapies, which are slow acting, time consuming, expensive and potentially dangerous with many other unpleasant adverse effects. With my medication, embodied in the form of a topical, over the counter treatment, even recalcitrant cases of athlete's foot can be cured with a few periodic applications of my medicine. Instead of months of antibiotic therapy, administered by a dermatologist, the sufferer can cure the condition themselves, with a safe, inexpensive and astonishingly power medicine, such as mine.

While my above description includes many specificities, these should not be regarded as limitations on the invention, but rather as an exemplification of certain preferred embodiments.

Accordingly, the scope of the invention should not be determined by these illustrated embodiments, but by the appended claims, and their legal equivalents.

What is claimed is:

1. A method of treating deep tissue, or systemic fungal diseases comprising:
    administration to an area of disease a suitable carrier containing a primary anti-infective agent obtainable from capsicum pepper, or an equivalent in a therapeutically effective amount.

2. A method of treating systemic fungal diseases selected from the group consisting of blastomycosis, coccidioidomycosis, entomophthoromycosis, or paracoccidioidomycosis comprising:
    administration to an area of disease a suitable carrier containing a primary anti-infective agent obtainable from pepper, or an equivalent in a therapeutically effective amount.

3. A method of treating systemic fungal diseases selected from the group consisting of aspergillosis, candidiasis, cryptococcosis, or histoplasmosis comprising:
    systemic administration to an area of disease a suitable carrier containing a primary anti-infective agent obtainable from pepper, or an equivalent in a therapeutically effective amount.

4. A method of treating fungal infections of the mucosa comprising:
    administration to an area of disease a suitable carrier containing a primary anti-infective agent obtainable from a pepper plant of the genus Capsicum, Peperoma, or species *Piper* retrofractum, *Piper longum*, or *Piper nigrum* in a therapeutically effective amount.

5. A method of treating the superficial manifestations of fungal disease in the areas of the body about the face, ear, mouth, neck, and below and deep tissue, or systemic fungal diseases comprising: administration to the area of disease a suitable carrier containing a primary anti-infective agent obtainable from pepper, or an equivalent wherein a therapeutically effective amount is a concentration similar to oleoresin or less.

6. A method of treating the superficial manifestations of fungal disease or systemic fungal diseases comprising:
    administration to the area of disease a suitable carrier containing a primary anti-infective agent obtainable from pepper, or an equivalent wherein a therapeutically effective amount is a concentration within the range of ground spice or oleoresin.

7. A method as in any one of claims 5 or 6, wherein the disease infects the feet.

8. A method as in any one of claims 5 or 6, wherein the disease infects the body area.

9. A method as in any one of claims 5 or 6, wherein the disease infects the crotch area.

10. The method of claim 6, wherein the disease infects the scalp.

11. A method as in any one of claims 1–6, wherein the disease is candidiasis.

12. A method as in any one of claims 1–6, wherein said agent is a synthetic.

13. A method as in any one of claims 2, 3, 5, or 6, wherein said pepper is a Capsicum.

14. A method as in any one of claims 1–6, wherein said agent is a capsaicinoid analog.

15. A method as in any one of claims 2, 3, 5, or 6, wherein said plant is *piperaceous*.

16. A method as in any one of claims 2, 3, 5, or 6, wherein said agent contains a piperidine constituent.

17. A method as in any one of claims 1–6, wherein said pepper is cayenne.

18. A method as in any one of claims 1–6, wherein said pepper is paprika.

19. A method as in any one of claims 1–6, wherein said pepper is black.

* * * * *